(12) United States Patent
Li et al.

(10) Patent No.: US 8,829,001 B2
(45) Date of Patent: Sep. 9, 2014

(54) DOPAMINE D3 RECEPTOR LIGANDS AND PREPARATION AND MEDICAL USES OF THE SAME

(75) Inventors: Jin Li, Beijing (CN); Rifang Yang, Beijing (CN); Rui Song, Beijing (CN); Hui Zhu, Beijing (CN); Ning Wu, Beijing (CN); Liuhong Yun, Beijing (CN); Ruibin Su, Beijing (CN); Rusheng Zhao, Beijing (CN)

(73) Assignee: The Institute of Pharmacology and Toxicology Academy of Military Medical Science P.L.A. China, Beijing (CN)

( * ) Notice: Subject to any disclaimer, the term of this patent is extended or adjusted under 35 U.S.C. 154(b) by 214 days.

(21) Appl. No.: 13/123,368

(22) PCT Filed: Sep. 28, 2009

(86) PCT No.: PCT/CN2009/001096
§ 371 (c)(1),
(2), (4) Date: Jun. 23, 2011

(87) PCT Pub. No.: WO2010/040274
PCT Pub. Date: Apr. 15, 2010

(65) Prior Publication Data
US 2011/0319423 A1    Dec. 29, 2011

(30) Foreign Application Priority Data

Oct. 10, 2008    (CN) .......................... 2008 1 0167089

(51) Int. Cl.
| | |
|---|---|
| *A61K 31/496* | (2006.01) |
| *A61K 31/506* | (2006.01) |
| *C07D 263/58* | (2006.01) |
| *C07D 277/68* | (2006.01) |
| *C07D 417/12* | (2006.01) |
| *C07D 413/12* | (2006.01) |
| *C07D 413/14* | (2006.01) |
| *C07D 417/14* | (2006.01) |

(52) U.S. Cl.
CPC ............ *A61K 31/496* (2013.01); *C07D 277/68* (2013.01); *C07D 263/58* (2013.01); *C07D 413/12* (2013.01); *C07D 413/14* (2013.01); *C07D 417/12* (2013.01); *C07D 417/14* (2013.01)
USPC .............. 514/252.19; 514/253.1; 514/254.02; 544/295; 544/364; 544/368

(58) Field of Classification Search
None
See application file for complete search history.

(56) References Cited

U.S. PATENT DOCUMENTS

| | | | |
|---|---|---|---|
| 4,863,951 A | 9/1989 | Peglion et al. | |
| 5,872,119 A | 2/1999 | Wermuth et al. | |
| 6,090,807 A | 7/2000 | Hellendahl et al. | |
| 6,358,955 B1 | 3/2002 | Thurkauf et al. | |
| 6,465,485 B1 | 10/2002 | Branch et al. | |
| 6,521,638 B1 | 2/2003 | Johnson et al. | |
| 6,602,867 B1 | 8/2003 | Starck et al. | |
| 6,673,800 B2 | 1/2004 | Koh et al. | |
| 2002/0156085 A1 | 10/2002 | Anand et al. | |
| 2005/0197343 A1 | 9/2005 | Gmeiner et al. | |
| 2007/0054918 A1 | 3/2007 | Braje et al. | |
| 2008/0113988 A1 | 5/2008 | Andres-Gil et al. | |
| 2008/0194539 A1 | 8/2008 | Gmeiner et al. | |
| 2008/0214542 A1 | 9/2008 | Capet et al. | |
| 2011/0251212 A1* | 10/2011 | Masui et al. ............. | 514/253.07 |

FOREIGN PATENT DOCUMENTS

| | | | |
|---|---|---|---|
| CA | 2574827 A1 | | 8/2005 |
| WO | 9504713 A1 | | 2/1995 |
| WO | 9510513 A1 | | 4/1995 |
| WO | 9743262 A1 | | 11/1997 |
| WO | 9806699 A1 | | 2/1998 |
| WO | 03028728 A1 | | 4/2003 |
| WO | 03051370 A1 | | 6/2003 |
| WO | 2007022936 A1 | | 3/2007 |
| WO | 2008/047883 | * | 4/2008 |
| WO | 2009/025265 | * | 2/2009 |

OTHER PUBLICATIONS

Vippagunta et al Advanced Drug Delivery Reviews, vol. 48, pp. 3-26 (2001).*
Luippold et al.Arch. Pharmacology, vol. 371, pp. 420-427 (2005).*
Rui Song et al., "YQA14: a novel dopamine D3 receptor antagonist that inhibits cocaine self-administration in rats and mice, but not in D3 receptor-knockout mice," Addiction Biology 17, 259-73, 2011.
Grundt et al., "Heterocyclic Analogues of N-(4-(4-(2,3-Dichlorophenyl)piperazin-1-yl)butyl)arylcarboxamides with Functionalized Linking Chains as Novel Dopamine D3 Receptor Ligands: Potential Substance Abuse Therapeutic Agents," J. Med. Chem, 2007, 50, 4135-4146.
Leopoldo et al., "Design, Synthesis, and Binding Affinities of Potential Positron Emission Tomography (PET) Ligands for Visualization of Brain Dopamine D3 Receptors," J. Med. Chem, 2006, 49, 358-365.
Blagg et al., Design and synthesis of a functionally selective D3 agonist and its in vivo delivery via the intranasal route, Bioorg Med Chem Lett, 2007, 17: 6691-6696.

(Continued)

*Primary Examiner* — Emily Bernhardt
(74) *Attorney, Agent, or Firm* — Banner & Witcoff, Ltd.

(57) ABSTRACT

The present invention relates to a novel piperazine derivative represented by Formula I having an activity for regulating dopamine D3 receptor, stereoisomers thereof, pharmaceutically acceptable salts or solvates, and a pharmaceutical composition comprising the compound, a process for preparing the same, and use thereof in the prevention or treatment of a disease associated with central nervous system dysfunction, such as Parkinson's disease, schizophrenia, drug addiction and relapse, as well as kidney protection and immunoregulation, or as a tool for researching D3R function or diseases associated with D3R dysfunction.

9 Claims, 3 Drawing Sheets

(56) References Cited

OTHER PUBLICATIONS

Boeckler et al., "Attenuation of 1-methyl-4-phenyl-1,2,3,6-tetrahydropyridine (MPTP) neurotoxicity by the novel selective dopamine D3-receptor partial agonist FAUC 329 predominantly in the nucleus accumbens of mice", Beichem Pharmacol, 2003, 66: 1025-1032.

Dubuffet et al., "Novel Benzopyrano[3,4-C]Pyrrole Derivatives as Potent and Selective Dopamine D3 Receptor Antagonists", Bioorg & Med Chem Lett, 1999, 9: 2059-2064.

Grundt et al., "Dopmine D3 Receptor Partial Agonists and Antagonists as Potential Drug Abuse Therapeutic Agents", J Med Chem, 2005, 45(11): 3663-3679.

Heidbreder, Christian, "Recent Advances in the Pharmacotherapeutic Management of Drug Dependence and Addiction", Curr Psychiatry Rev, 2005, (1): 45-67.

Heidbreder et al., "The role of central dopamine D3 receptors in drug addiction: a review of pharmacological evidence", Brain Res Rev, 2005, 49: 77-105.

Joyce, J.N. et al., "Dopamine D3 receptor antagonists as therapeutic agents", Drug Disc Today, 2005, 10(13): 917-925.

Leiberman, Abraham, "Depression in Parkinson's disease—a review", Acta Neuro Scand, 2006, 113: 1-8.

Moore, N.A. et al., "Behavioral Pharmacology of Olanzapine: A Novel Antipsychotic Drug", J Clin Psychiatry, 58(suppl 10): 37-44, (1997).

Suzuki, T. et al., "Studies on a New Nonsteroidal Antiinflammatory Agent II. A New Synthetic Mthod of 2-Substituted-5-benzothiazoleacetic Acids and Their Derivatives", 1974, 94(8): 891-897.

Xi, Z-X et al., "Levo-tetrahydroplamatine inhibits cocaine's rewarding effects: Experiments with self-administration and brain-stimulation reward in rats", Neuropharmacology, 2007, 53: 771-782.

Song et al., "Blockade of D3 Receptors by YQA14 Inhibits Cocaine's Rewarding Effects and Relapse to Drug-Seeking Behavior in Rats," Neuropharmacology, Feb. 2014;77:398-405; Epub 2013 Oct 28.

Song et al., "Dopamine D3 receptor deletion or blockade attenuates cocaine-induced conditioned place preference in mice," Neuropharmacology 72, 82-87, 2013.

Office Action for JP No. 2011-530350 mailed Nov. 5, 2013, 5 pages, including English translation.

* cited by examiner

DOPAMINE D3 RECEPTOR LIGANDS AND PREPARATION AND MEDICAL USES OF THE SAME

CROSS REFERENCE TO RELATED APPLICATIONS

This is a U.S. National Phase Application under 35 U.S.C. §371 of International Application No. PCT/CN2009/001096 filed Sep. 28, 2009, which claims priority to Chinese Application No. 200810167089.5, filed Oct. 10, 2008, the entire contents of which are incorporated herein by reference.

TECHNICAL FIELD

The present invention relates to a novel piperazine derivative of formula I having dopamine D3 receptor (D3R) regulating activity, or stereoisomers, pharmaceutically acceptable salts and solvates of the same, to a process for preparing the same, to use thereof in the prevention or treatment of diseases associated with central nervous system disorders, such as Parkinson's disease, schizophrenia, drug addiction and relapse, as well as for kidney protection and immunoregulation, or use as a tool for researching D3R function and diseases associated with D3R dysfunction, and to a pharmaceutical composition comprising such compounds.

BACKGROUND ART

Dopamine (DA) is an important neuromediator in central nervous system. The disbalance of DA nerves in brain may result in schizophrenia, Parkinson's disease, drug addiction and relapse, attention deficit or sexual dysfunction.

In 1990, Sokoloff et al found dopamine D3 receptor (D3R), and found it has 50% amino acid sequence homology in comparison with D2R, and further identified the specific typing of dopamine receptor. D3R is selectively distributed in marginal brain area, such as nucleus accumbens, Callejia island, olfactory tubercle. Some current research reports show that D3R is closely associated with many neurosises, such as schizophrenia, Parkinson's disease, drug dependence (or drug addiction), any forms of stress, anxiety, and somnipathy. In addition, D3R is associated with physiologic functions such as kidney function and immunoregulation.

In investigating the physiological functions of D3R and its correlation with central diseases, kidney dysfunction and immunological disorders, the research of D3R ligands is also a hotspot of drug studying. D3R ligands can be divided into D3R preferential ligands and D3R selective ligands according to their selectivity, or divided into D3R agonists, D3R partial agonists and D3R antagonists.

Currently, D3R ligands having relatively high affinity and selectivity have been disclosed in many technical reports. According to their chemical structure, the present D3R ligands mainly include 2-aminoindanes (WO95/04713), 2-aminotetrahydronaphthalenes (EP-A286516), tetrahydroisoquinolines (WO 97/43262, WO98/06699, U.S. Pat. No. 6,465,485 B1), benzoazepines (CN 01821985.3), dihydroindolines (U.S. Pat. No. 6,521,638B1), aryl piperazine derivatives (FR2878524), heterocyclic amides (EP 1749529), sulfonamides (US2007054918), benzothiophenes (WO95/10513), isoxazole derivatives (U.S. Pat. No. 6,673,800B2), substituted imidazoles (U.S. Pat. No. 6,358,955B1), triazoles (U.S. Pat. No. 6,602,867B1, WO2007022936), pyrimidinylpiperazine derivatives (CA2574827), etc. In general, there are groups of arylformamides, bioisosteres with arylformamido group, and 1,2,3,4-tetrahydronaphthalene-2-amine and analogs thereof, in which the group of arylformamides is the biggest group, in which the aryl can be of various types, the amino moiety can be mainly piperazine or tetrahydroisoquinoline, and amino can be linked to the arylformamido via four methylene groups or an equivalent linking chain (YANG Rifang, YUN Liuhong, "Advance in research of dopamine D3 receptor selective ligands, *Progesses in Medicinal Chemistry* 5, Edited by PENG Sixun, Chemical Industry Press, Beijing, 2007, pp 90-108).

Some D3R selective ligands show potential values for developing new drugs with D3R as the target in corresponding animal models and clinic trials. For example, Pramipexole (A Lieberman. *Acta Neurol Scand,* 2006, 113: 1), FAUC329 (F Boeckler, et al. *Biochem Phamacol,* 2003, 66(6): 1025), and BP897 (U.S. Pat. No. 5,872,119) disclose excellent neuroprotective effects in macaque model of Parkinson's disease; D3R preferential ligands S33138, A437203 (T Dubuffer, et al. *Bioorg Med Chem Lett,* 1999, 9(14): 2059; J F Joyce, M J Millan. *Drug Disc Today,* 2005, 10: 917) have entered phase II clinical test for treatment of schizophrenic; BP897 (C A Heidbreder. *Curr Psychiatry Rev,* 2005, 1: 45), SB277011A (C A Heidbreder, et al. *Brain Res Rev,* 2005, 49(1): 77) and NGB2904 (P Grundt, et al. *J Med Chem,* 2005, 48(13): 917) have been drawing many attentions in studying of drug addiction mechanism and development of drugs for treatment of drug addiction and relapse, in which BP897 as smoking deterrent is currently in phase II clinical test. Other reports mention that D3R agonist can be used for prevention of male sexual dysfunction (WO2003/051370, J Bragg, et al. *Bioorg Med Chem Lett,* 2007, 17: 6691).

Recent investigations indicate that D3R preferential ligands are more effective in prevention of drug abuse and relapse without exhibiting toxic and side effects of D2R ligands (Z-X Xi, et al. *Neuropharmacology,* 2007, 53: 771).

At present, there is still a need to search for novel compounds as dopamine D3 receptor ligands for clinical uses.

CONTENTS OF THE INVENTION

The inventors of the present invention found by research a compound of formula I having a function for regulating D3R, this compound can be used for prevention or treatment of schizophrenia, Parkinson's disease, drug dependence (or drug addiction) and relapse, various mental strain, anxiety, somnipathy and male sexual dysfunction, as well as kidney protection and immunoregulation. Some researches indicate that the compound of formula I has function of regulating D3R. Further synthesis and researches indicate that pharmaceutically acceptable salts of the derivatives of the present invention formed with a suitable inorganic acid or organic acid or with an inorganic base or organic base also have functions of regulating D3R. The present invention is completed based on the above findings.

SUMMARY OF THE INVENTION

The first aspect of the present invention relates to a compound of formula I having a function for regulating D3R,

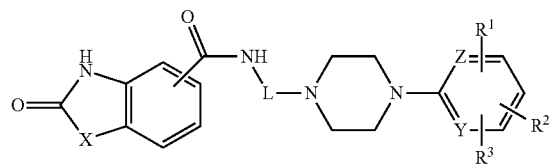

I or its tautomers, its racemates or optical isomers, its pharmaceutically acceptable salts or solvates, wherein:

L is $CH_2CH_2CH_2CH_2$, cis- or trans-$CH_2CH=CHCH_2$, or trans-cyclohexanyl-4-ethyl;

$R^1$, $R^2$, and $R^3$ each are independently H, halogen (F, Cl, Br, or I), alkyl, substituted alkyl, alkenyl, substituted alkenyl, phenyl, substituted phenyl, heteroaryl, substituted heteroaryl, $C_1$-$C_6$ alkyloxy, $C_5$-$C_{10}$ aryloxy, substituted aryloxy, $C_1$-$C_6$ alkylamino, $C_5$-$C_{10}$ arylamino, substituted arylamino, di-($C_1$-$C_6$ alkyl)amino, di-($C_5$-$C_{10}$aryl)amino, di-(substituted aryl)amino, $C_{1-10}$ hydrocarbonylcarbonyloxy, $C_{6-10}$ arylacyloxy, $C_{1-10}$ hydrocarbonylamido, $C_{6-10}$ arylamido, carboxyl, $C_{1-10}$ hydrocarbonyloxycarbonyl, $C_{6-10}$ aryloxycarbonyl, carbamoyl, $C_{1-10}$ hydrocarbonylcarbamoyl, or $C_{6-10}$ arylcarbamoyl; wherein the heteroaryl ring is a monocyclic or condensed aromatic ring having 1-3 heteroatoms selected from N, O or S, the substituents of each group having substituents are independently selected from halogen, hydroxyl, cyano, nitro, $C_{1-6}$ alkyl, $C_{1-6}$ alkyloxy, $C_{1-6}$ alkylthio, mono-, di- or tri-halogen substituted $C_{1-6}$ alkyl, amino, $C_{1-6}$ alkylamino, $C_{1-10}$ hydrocarbonylcarbonyloxy, $C_{1-10}$ hydrocarbonylamido, $C_{6-10}$ arylacyloxy or $C_{6-10}$ arylamido; or $R^1$ and $R^3$ are attached together to form a 5-, 6- or 7-membered ring;

X is O or S; Y and Z, the same or different, each are CH or N; and the carbonyl may be at 4-, 5-, 6-, or 7-position of the benzoxazolin-2-one or benzthiazolin-2-one.

Specifically, the first aspect of the present invention provides a compound of formula I,

I or its tautomers, its racemates or optical isomers, its pharmaceutically acceptable salts or solvates, wherein:

L is —$CH_2CH_2CH_2CH_2$—, cis- or trans-$CH_2CH=CHCH_2$—, or trans-cyclohexyl-4-ethyl;

$R^1$, $R^2$, and $R^3$ each are independently H, halogen (F, Cl, Br, or I), $C_1$-$C_6$ alkyl, substituted $C_1$-$C_6$ alkyl, $C_1$-$C_6$ alkenyl, substituted $C_1$-$C_6$ alkenyl, phenyl, substituted phenyl, heteroaryl, substituted heteroaryl, $C_1$-$C_6$ alkyloxy, $C_5$-$C_{10}$ aryloxy, substituted $C_5$-$C_{10}$ aryloxy, $C_1$-$C_6$ alkylamino, $C_5$-$C_{10}$ arylamino, substituted arylamino, di-($C_1$-$C_6$ alkyl)amino, di-($C_5$-$C_{10}$aryl)amino, di-(substituted$C_5$-$C_{10}$aryl)amino, $C_{1-10}$ hydrocarbonylcarbonyloxy, $C_{6-10}$arylacyloxy, $C_{1-10}$hydrocarbonylamido, $C_{6-10}$arylamido, carboxyl, $C_{1-10}$hydrocarbonyloxycarbonyl, $C_{6-10}$ aryloxycarbonyl, carbamoyl, $C_{1-10}$ hydrocarbonylcarbamoyl, or $C_{6-10}$ arylcarbamoyl; wherein the heteroaryl ring is a monocyclic or condensed aromatic ring having 1-3 heteroatoms selected from N, O or S, the substituents of each group having substituents are independently selected from halogen, hydroxyl, cyano, nitro, $C_{1-6}$ alkyl, $C_{1-6}$ alkyloxy, $C_{1-6}$ alkylthio, mono-, di- or tri-halogen substituted $C_{1-6}$ alkyl, amino, $C_{1-6}$ alkylamino, $C_1$-10 hydrocarbonylcarbonyloxy, $C_{1-10}$hydrocarbonylamido, $C_{6-10}$ arylacyloxy or $C_{6-10}$-arylamido; or $R^1$ and $R^3$ are attached together to form a 5-, 6- or 7-membered ring;

X is O or S;

Y and Z, the same or different, are each C or N;

The carbonyl may be at 4-, 5-, 6-, or 7-position of the benzoxazolin-2-one or benzthiazolin-2-one.

The compound of formula I according to any one item of the first aspect of the present invention, or its tautomers, its racemates or optical isomers, its pharmaceutically acceptable salts or solvates, wherein L is —$CH_2CH_2CH_2CH_2$—, cis- or trans-$CH_2CH=CHCH_2$—, or trans-cyclohexyl-4-ethyl. In one embodiment of the first aspect of the present invention, L is —$CH_2CH_2CH_2CH_2$—, or cis- or trans-$CH_2CH=CHCH_2$—. In one embodiment of the first aspect of the present invention, L is —$CH_2CH_2CH_2CH_2$—. In one embodiment of the first aspect of the present invention, L is cis- or trans-$CH_2CH=CHCH_2$—.

The compound of formula I according to any one item of the first aspect of the present invention, or its tautomers, its racemates or optical isomers, its pharmaceutically acceptable salts or solvates, wherein $R^1$, $R^2$, and $R^3$ each are independently H, halogen (F, Cl, Br, or I), $C_1$-$C_6$ alkyl, substituted $C_1$-$C_6$ alkyl, $C_1$-$C_6$ alkenyl, substituted $C_1$-$C_6$ alkenyl, phenyl, substituted phenyl, heteroaryl, substituted heteroaryl, $C_1$-$C_6$ alkyloxy, $C_5$-$C_{10}$ aryloxy, substituted $C_5$-$C_{10}$ aryloxy, $C_1$-$C_6$ alkylamino, $C_5$-$C_{10}$ arylamino, substituted arylamino, di-($C_1$-$C_6$ alkyl)amino, di-($C_5$-$C_{10}$aryl)amino, di-(substituted $C_5$-$C_{10}$aryl)amino, $C_{1-10}$ hydrocarbonylcarbonyloxy, $C_{6-10}$ arylacyloxy, $C_{1-10}$hydrocarbonylamido, $C_{6-10}$arylamido, carboxyl, $C_{1-10}$ hydrocarbonyloxycarbonyl, $C_{6-10}$ aryloxycarbonyl, carbamoyl, $C_{1-10}$ hydrocarbonylcarbamoyl, or $C_{6-10}$ arylcarbamoyl; wherein the heteroaryl ring is a monocyclic or condensed aromatic ring having 1-3 heteroatoms selected from N, O or S, the substituents of each group having substituents are independently selected from halogen, hydroxyl, cyano, nitro, $C_{1-6}$ alkyl, $C_{1-6}$ alkyloxy, $C_{1-6}$ alkylthio, mono-, di- or tri-halogen substituted $C_{1-6}$ alkyl, amino, $C_{1-6}$ alkylamino, $C_{1-10}$ hydrocarbonylcarbonyloxy, $C_{1-10}$hydrocarbonylamido, $C_{6-10}$ arylacyloxy or $C_{6-10}$ arylamido. In one embodiment of the first aspect of the present invention, $R^1$, $R^2$, and $R^3$ each are independently H, F, Cl, Br, I, $C_1$-$C_6$ alkyl, or $C_1$-$C_6$ alkyloxy. In one embodiment of the first aspect of the present invention, $R^1$, $R^2$, and $R^3$ each are independently H, F, Cl, Br, $C_1$-$C_4$ alkyl, or $C_1$-$C_4$ alkyloxy. In one embodiment of the first aspect of the present invention, $R^1$, $R^2$, and $R^3$ each are independently H, F, Cl, methyl, ethyl, methyloxy, or ethyloxy.

The compound of formula I according to any one item of the first aspect of the present invention, or its tautomers, its racemates or optical isomers, its pharmaceutically acceptable salts or solvates, wherein X is O or S. In one embodiment of the first aspect of the present invention, X is O. In one embodiment of the first aspect of the present invention, X is S.

The compound of formula I according to any one item of the first aspect of the present invention, or its tautomers, its racemates or optical isomers, its pharmaceutically acceptable salts or solvates, wherein Y and Z each are independently C or N. In one embodiment of the first aspect of the present invention, Y is C. In one embodiment of the first aspect of the present invention, Z is C. In one embodiment of the first aspect of the present invention, both Y and Z are C.

The compound of formula I according to any one item of the first aspect of the present invention is selected from:
N-{4-[4-(5-chloro-2-methylphenyl)piperazinyl]butyl}-benzoxazolin-2-one-5-carboxamide;
N-{4-[4-(5-chloro-2-methylphenyl)piperazinyl]butyl}-benzoxazolin-2-one-6-carboxamide;
N-{4-[4-(2-methyloxyphenyl)piperazinyl]butyl}-benzoxazolin-2-one-5-carboxamide;
N-{4-[4-(2-methyloxyphenyl)piperazinyl]butyl}-benzoxazolin-2-one-6-carboxamide;
N-{4-[4-(5-chloro-2-methylphenyl)piperazinyl]-trans-2-buten-1-yl}-benzoxazolin-2-one-6-carboxamide;
N-{4-[4-(5-chloro-2-methylphenyl)piperazinyl]-cis-2-buten-1-yl}-benzoxazolin-2-one-5-carboxamide;
N-{4-[4-(2-methyloxyphenyl)piperazinyl]-trans-2-buten-1-yl}-benzoxazolin-2-one-5-carboxamide;
N-{4-[4-(2-methyloxyphenyl)piperazinyl]-trans-2-buten-1-yl}-benzoxazolin-2-one-6-carboxamide;
N-{4-[4-(2-methyloxyphenyl)piperazinyl]butyl}-benzothiazolin-2-one-6-carboxamide;
N-{4-[4-(5-chloro-2-methylphenyl)piperazinyl]butyl}-benzothiazolin-2-one-6-carboxamide;
N-{4-[4-(2-methyloxyphenyl)piperazinyl]-trans-2-buten-1-yl}-benzothiazolin-2-one-6-carboxamide;
N-{4-[4-(2-methyloxyphenyl)piperazinyl]butyl}-benzothiazolin-2-one-5-carboxamide; or
N-{4-[4-(5-chloro-2-methylphenyl)piperazinyl]butyl}-benzothiazolin-2-one-5-carboxamide,
or their tautomers, their racemates or optical isomers, their pharmaceutically acceptable salts or solvates.

The second aspect of the present invention relates to use of a compound of formula I according to any one item of the first aspect of the present invention, or its tautomers, its racemates or optical isomers, its pharmaceutically acceptable salts or solvates, in the manufacture of a medicament for the prevention or treatment of schizophrenia, Parkinson's disease, drug dependence (or drug addiction) and relapse, any forms of stress, anxieties, sleep disorders and male sexual dysfunction, as well as for kidney protection and immunoregulation, or as a tool for researching D3R function or diseases associated with D3R dysfunction.

The third aspect of the present invention provides use of a compound of formula I according to any one item of the first aspect of the present invention, or its tautomers, its racemates or optical isomers, its pharmaceutically acceptable salts or solvates, in the manufacture of a medicament having an activity for regulating dopamine D3 receptor.

The fourth aspect of the present invention provides a pharmaceutical composition, comprising a compound of formula I according to any one item of the first aspect of the present invention, or its tautomers, its racemates or optical isomers, its pharmaceutically acceptable salts or solvates, and a pharmaceutically acceptable carrier or excipient. According to this aspect, the present invention further provides use of the pharmaceutical composition in the manufacture of a medicament for the prevention or treatment of schizophrenia, Parkinson's disease, drug dependence (or drug addiction) and relapse, any forms of stress, anxieties, sleep disorders and male sexual dysfunction, as well as for kidney protection and immunoregulation, or as a tool for researching D3R function or diseases associated with D3R dysfunction.

The fifth aspect of the present invention provides a method for the prevention or treatment of a disease associated with D3R dysfunction, such as schizophrenia, Parkinson's disease, drug dependence (or drug addiction) and relapse, any forms of stress, anxieties, sleep disorders and male sexual dysfunction, as well as kidney dysfunction and immunological disorders, comprising administering to a subject in a need thereof a preventive and/or therapeutically effective amount of a compound of formula I according to any one item of the first aspect, or its tautomers, its racemates or stereoisomers, its pharmaceutically acceptable salts.

The sixth aspect of the present invention provides a process for preparing a compound of formula I according to any one item of the first aspect of the present invention, or its tautomers, its racemates or optical isomers, its pharmaceutically acceptable salts or solvates, comprising the following steps:

a) converting a carboxylic acid compound of formula II:

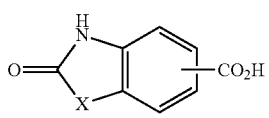

II into an acyl chloride compound of formula IIa:

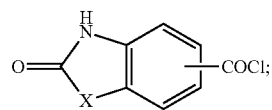

IIa b) In the presence of a suitable base, reacting the acyl chloride compound of formula IIa obtained in the step a) with an amine compound of formula III:

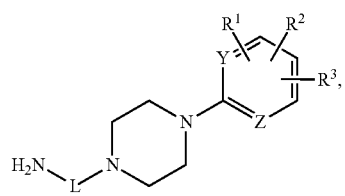

III to obtain a compound of formula I:

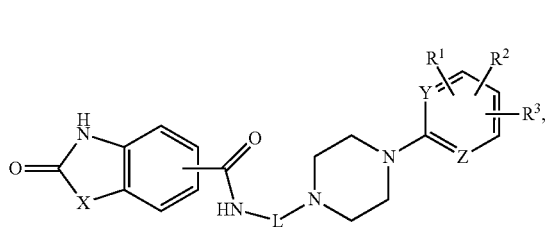

I wherein the definitions of symbols are the same as given for the compound of formula I according to any one item of the first aspect of the present invention.

According to the method of the sixth aspect of the present invention, the carboxylic acid compound of formula II is obtained by reacting a carboxylic acid compound of formula IV:

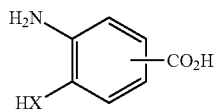

IV with a compound represented by ClCO$_2$R,
wherein the definitions of symbols are the same as given for the compound of formula I according to any one item of the first aspect of the present invention.

According to the method of the sixth aspect of the present invention, the amine compound of formula III is obtained by reacting a compound of formula V:

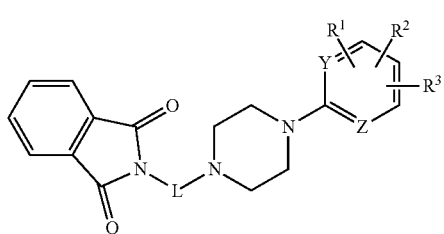

V in the presence of a suitable agent (such as hydrazine hydrate),
wherein the definitions of symbols are the same as given for the compound of formula I according to any one item of the first aspect of the present invention.

DETAILED DESCRIPTION OF THE INVENTION

All documents as cited in the present invention are incorporated in the description by reference, and if the meanings expressed in these documents are different from the present invention, the expressions in the present invention shall prevail.

In addition, the terms and phrases used in the present invention have common meanings as well known by those skilled in the art. Nevertheless, in the present invention, it is desired to further illustrate and explain these terms and phrases in a more detailed way, if the mentioned terms and phrases have meanings different from their common meanings, the meanings expressed in the present invention shall prevail.

In the present invention, the used terms "halogen", "halo", "Hal" or "halogeno" refers to fluorine, chlorine, bromine and iodine.

In the present invention, the used terms "alkyl", "alkenyl" and "alkynyl" have common meanings well known in the art, they are straight or branched hydrocarbonyl groups, such as but not limited to methyl, ethyl, propyl, isopropyl, n-butyl, sec-butyl, tert-butyl, allyl, propenyl, propinyl, and the "alkyl", "alkenyl" and "alkynyl" can also be collectively called "hydrocarbonyl" or "aliphatic hydrocarbonyl".

As used in the text, the term "substituted or unsubstituted C$_1$-C$_6$ alkyl" refers to substituted or unsubstituted alkyl having a designated number of carbon atoms, its examples include but are not limited to: methyl, ethyl, propyl, isopropyl, butyl, tert-butyl, pentyl, neopentyl, hexyl.

As for Y and Z in the compound of formula I, they can be independently C or N. Those skilled in the art would understand that Y and Z herein should meet the valence requirements of 6-membered ring. For example, when R$^1$, R$^2$ and R$^3$ are all hydrogen, if Y and Z are carbon, the 6-membered ring forms a beneze ring, so that Y or Z is —CH— atomic group; if Y is nitrogen, Z is carbon, the 6-membered ring forms a pyridine ring, so that Y is —N— atomic group, Z is —CH— atomic group. For another example, when Y is nitrogen and Z is carbon, if R$^1$ is halogen, and R$^2$ and R$^3$ are hydrogen, the halogen can be linked to Z to form a —CCl— atomic group.

According to the first aspect of the present invention, in the compound of formula I, R$^1$, R$^2$, and R$^3$ each are preferably H, F, Cl, Br, methyl, ethyl, methyloxy, ethyloxy, dimethylamino, diethylamino, carbamoyl, or phenyloxy;

L is preferably —CH$_2$CH$_2$CH$_2$CH$_2$—, or trans —CH$_2$CH=CHCH$_2$—;

X is preferably O or S; Y and Z each are preferably CH or N.

According to another aspect of the present invention, in the compound of formula I, R$^1$, R$^2$, and R$^3$ each are preferably 5-chloro-2-methyl, 2,3-dichloro, or 2-methyloxy;

L is preferably —CH$_2$CH$_2$CH$_2$CH$_2$—, or trans —CH$_2$CH=CHCH$_2$—;

X is preferably O; and Y and Z each are preferably N.

The compounds of formula I according to the present invention are preferably the compounds of the following examples.

In the preferable embodiments of the present invention, the compound is N-{4-[4-(5-chloro-2-methylphenyl)piperazinyl]butyl}-benzoxazolin-2-one-5-carboxamide and N-{4-[4-(5-chloro-2-methyl-phenyl)piperazinyl]butyl}-benzoxazolin-2-one-6-carboxamide.

According to the teaching of the present invention, the compound of formula I of the invention can be synthesized by known methods and technologies in the art.

In one embodiment of the process for preparing a compound of formula I, the compound is prepared by converting a corresponding carboxylic acid II into an acyl chloride, then reacting with a corresponding amine III in the presence of an deacidificating agent; or by a direct dehydration of a mixture of a corresponding carboxylic acid II and a corresponding amine III with a condensing agent such as carbodiimide (e.g., N,N'-dicyclohexylcarbodiimide) in the presence of 1-hydroxy-benzotriazole, in which the carboxylic acid II is obtained by a thermal cyclization reaction between a carboxylic acid IV with adjacently substituted amino and hydroxyl or mercapto and a chloroformic ester in the presence of a deacidifying agent; and the amine III is prepared by reacting a corresponding phthalimide V and hydrazine hydrate, wherein

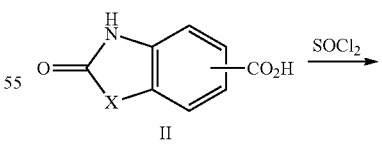

II

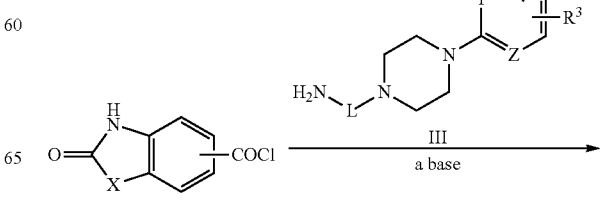

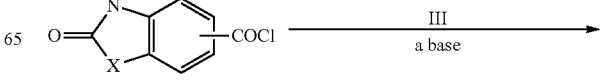

III

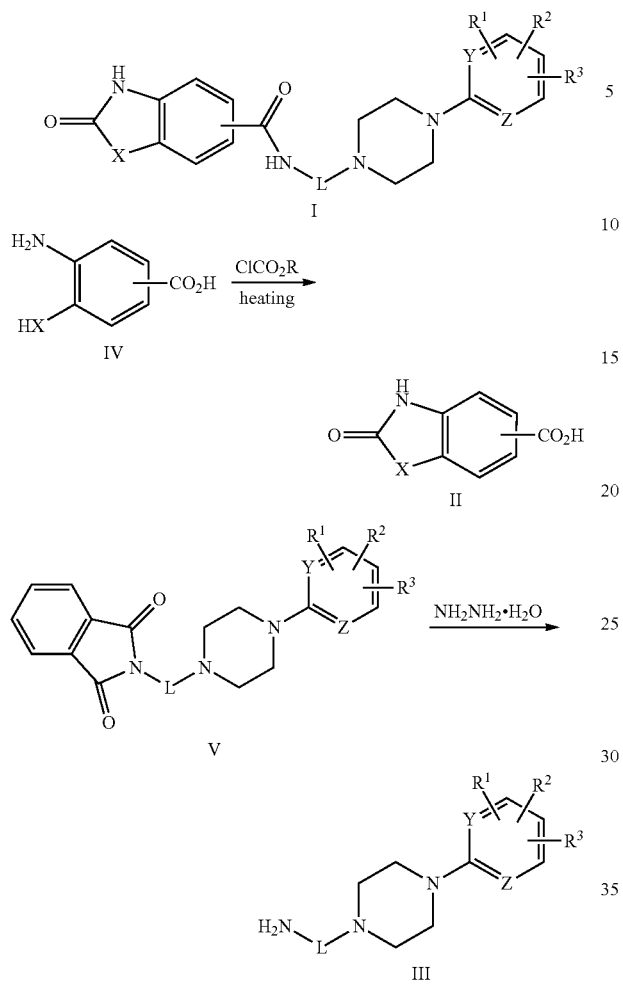

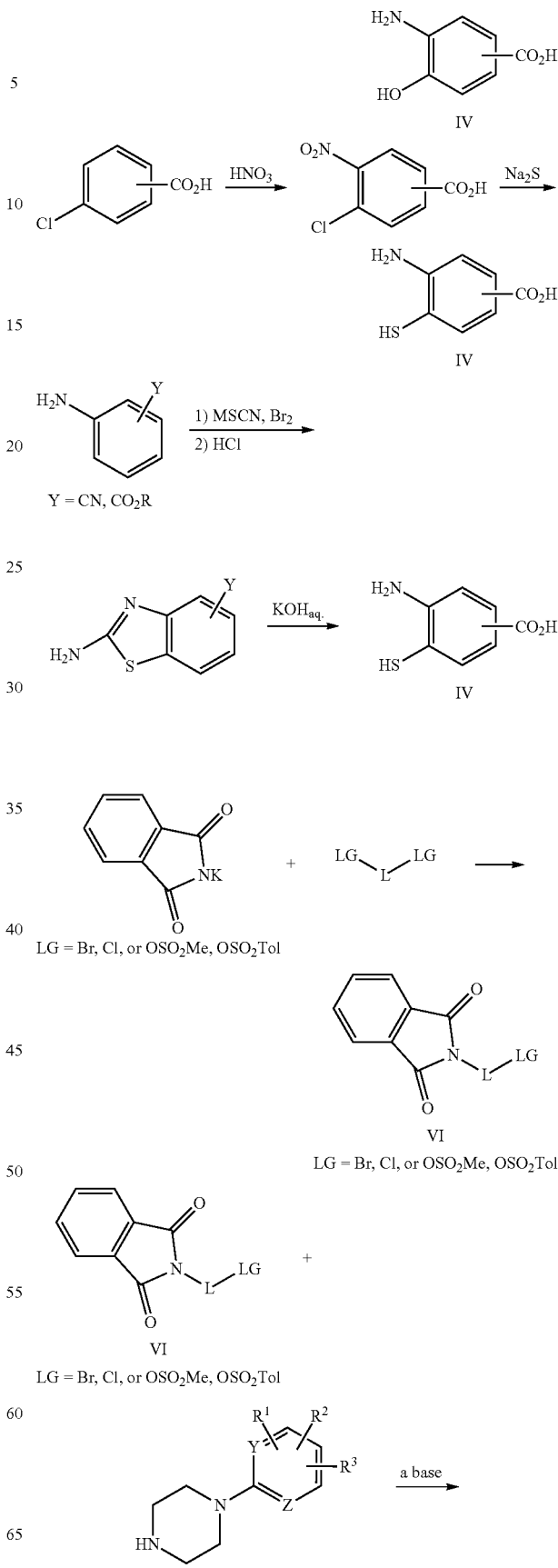

the carboxylic acid IV is prepared by nitrating a corresponding hydroxybenzoic acid, separating to obtain a benzoic acid adjacently substituted with nitro and hydroxy, then reducing to obtain a benzoic acid adjacently substituted with hydroxy and amino (IV); or by nitrating a corresponding chlorobenzoic acid, separating to obtain a benzoic acid adjacently substituted with chloro and nitro, then reducing and substituting with sodium sulfide to form a benzoic acid adjacently substituted with amino and mercapto (IV) (Tadayuki Suzuki et al, J. Pharmacy, 1974, 94:891-897); or by converting an aminobenzonitrile or aminobenzoic acid into a thiocyanobenzoic acid, cyclizating to form 2-aminobenzothiazole, then hydrolyzing in the presence of a base to form a benzoic acid adjacently substituted with amino and mercapto (IV); while the phthalimide V is prepared by reacting a corresponding halide or active ester VI with a corresponding arylpiperazine, in which the halide or active ester VI can be synthesized by reacting pththalimide potassium salt with a corresponding dichloride or active ester.

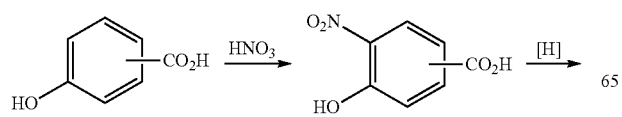

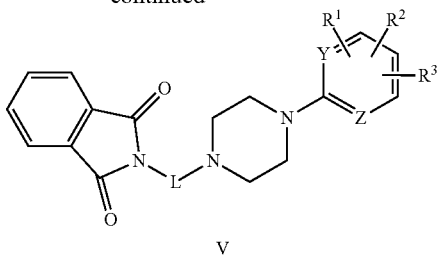

V

In the method for synthesizing a compound of formula I of the present invention, all used raw materials can be prepared according to the prior art, or prepared according to the methods known in the documents in the prior art, or commercially available. The intermediates, raw materials, reagents and reaction conditions used in the above reaction scheme all can be modified by those skilled in the art. In addition, those skilled in the art can also synthesized other compounds of formula I not enumerated in the present invention according to the method of the second aspect of the present invention.

According to the present invention, the term "diseases associated with D3R function disorder" refers to diseases directly or indirectly caused by dopamine D3 receptor function disorder, such as schizophrenia, Parkinson's disease, drug abuse (or drug addiction) and relapse, any forms of stress, anxieties, sleep disorders and male sexual dysfunction, as well as disorders of kidney function or immunologic function induced thereby.

According to the present invention, the pharmaceutically acceptable salt of the compound of formula I can be an acid addition salt or a salt formed with a base. The examples of the acid addition salt can be inorganic salts such as but not limited to hydrochlorides, sulfates, phosphates, hydrobromides; or organic salts such as but not limited to acetates, oxalates, citrates, glyconates, succinates, tartrates, tosylates, mesylates, benzoates, lactates, maleates; the examples of the salt formed with the compound of formula I and a base can be alkaline metal salts such as but not limited to lithium salts, sodium salts and potassium salts; alkaline earth metal salts such as but not limited to calcium salts and magnesium salts; organic alkali salts such as but not limited to diethanolamine salts and choline salts; or chiral alkali salts such as but not limited to alkylphenylamine salts.

The solvates of the compound of the present invention can be hydrates or comprise other crystalline solvent such as alcohols such as ethanol.

According to the present invention, the compound of formula I can have cis/trans isomers. The present invention relates to these cis- and trans-isomers and mixtures thereof. If desired, a single stereoisomer can be prepared by conventional resolution of mixture, or by stereoselective synthesis. If there is a mobile hydrogen atom, the compound of formula I of the present invention can also be its tautomers.

According to the present invention, the compound of formula I or stereoisomers can be used in the manufacture of a medicament for prevention or treatment of diseases associated with D3R function disorder, such as schizophrenia, Parkinson's disease, drug abuse (or drug addiction) and relapse, any forms of stress, anxieties, sleep disorders and male sexual dysfunction, as well as disorders of kidney function or immunologic function induced thereby. The medicament can be applied to animals, preferably mammals, especially a human.

The present invention also relates to a pharmaceutical composition comprising an effective amount of at least one compound of the Formula I or pharmaceutically acceptable salts and/or stereoisomers thereof as an active ingredient and a conventional pharmaceutically acceptable excipient or adjuvant. Usually, the pharmaceutical composition of the present invention comprises 0.1-90 wt % a compound of formula I and/or physiologically acceptable salt thereof. The pharmaceutical composition can be prepared by a known method in the art. If desired, an administration form or dosage form suitable for human use can be prepared by combining a compound of formula I and/or stereoisomer thereof with one or more solid or liquid pharmaceutically acceptable excipient and/or adjuvant.

The compound of formula I or a pharmaceutical composition comprising the same according to the present invention can be administered in unit dosage form via intestinal administration or parenteral administration, such as oral administration, intramuscular injection, subcutaneous injection, nasal administration, oral mucous administration, transdermal administration, intraperitoneal administration or rectal administration. The dosage form can be tablets, capsules, drop pills, aerosol, pills, powders, solutions, suspensions, emulsions, granules, liposomes, transdermal agents, buccal tablets, suppositories, lyophilized injection powder, can be normal preparations, sustained release preparations, controlled release preparations and various micropowder administration systems. In order to obtain tablets as unit dosage form, various carriers known in the art can be used. The examples of carriers are diluents and absorbents, such as starches, dextrins, calcium sulfates, lactose, mannitol, sucrose, sodium chloride, glucose, urea, calcium carbonate, kaolin, microcrystalline cellulose, aluminum silicate; wetting agents and binders, such as water, glycerol, polyethylene glycol, ethanol, propanol, starch paste, dextrin, syrup, honey, glucose solution, acacia mucilage, gelatin paste, carboxymethylcellulose sodium, shellac, methylcellulose, potassium phosphate, polyvinylpyrrolidone, disintegrating agents, such as dried starch, alginate, powdered agar, laminarin, sodium hydrogen carbonate and citric acid, calcium carbonate, polyoxyethylene sobitol fatty acid ester, sodium dodecyl sulfate, methylcellulose, ethylcellulose; disintegration inhibitors, such as sucrose, tristearin, cocoa butter, hydrogenated oil; absorption enhancers, such as quaternary ammonium salt, sodium dodecyl sufate; lubricants, such as talc powder, silica, corn starch, stearates, boric acid, liquid paraffin, polyethylene glycol. The tablets can further form coated tablets, such as sugar coated tablets, film coated tablets, enteric-coated tablets, or bilayer tablets or multilayer tablets. In order to obtain pills as the unit dosage form, various carriers known in the art can be used. The examples of these carriers can be diluents and absorbents, such as glucose, lactose, starch, cocoa butter, hydrogenated vegetable oil, polyvinylpyrrolidone, Gelucire, kaolin, talc powder, etc.; binder such as gum arabic, tragacanth gum, gelatin, ethanol, honey, liquid sugar, rice paste or panada; disintegrating agents, such as powdered agar, dried starch, alginate, sodium dodecyl sulfate, methylcellulose, ethylcellulose. In order to obtain suppositories as the dosage form, various carriers known in the art can be used. The examples of these carriers can be polyethylene glycol, lecithine, cocoa butter, fatty alcohols, esters of fatty alcohols, gelatin, semi-synthesized glycerides. In order to obtain capsules as the dosage form, an effective amount of a compound of formula I or stereoisomer thereof is mixed with the above various carriers, and the resultant mixture is filled into hard gelatin capsules or soft capsules. An effective amount of a compound of formula I or stereoisomer thereof can also form microcapsules, be suspended in aqueous media to form suspensions, be filled in hard capsules, or form injections. In order to obtain injection preparations as unit dosage form, such as solutions, emulsions, lyophilized powder injection, and suspensions, conventional diluents in the art can be used, such as water, ethanol, polyethylene glycol, 1,3-propanediol, ethoxylated isooctadecanol, multi-oxidized isooctadecanol, polyoxyethylene sorbitol fatty acid esters. In addition, in order to obtain isotonic injection solutions, a suitable amount of sodium chloride, glucose or glycerol can be added to injection preparations. Further, other conventional solvents, buffers, pH regulators can also be added.

Moreover, if desired, other materials such as coloring agents, preservatives, flavoring agents, correctants, sweetening agents can also be added to these pharmaceutical preparations.

The dose of a compound of formula I or stereoisomer according to the present invention depends on many factors, such as nature and severity of diseases to be prevented or treated, gender, age, body weight and individual reactions of patients or animals, specific compound to be used, administration routes and frequency. The dose can be of single dose form, or multi-dose forms such as 2, 3 or 4 dose forms.

In the present invention, the term "composition" refers to a product comprising designated amounts of designated ingredients, and any products directly or indirectly obtained by combining various designated ingredients of designated amounts.

The actual dose level of various active ingredients in a pharmaceutical composition of the present invention can be varied so that the resultant amount of active compounds can lead to desired therapeutical reactions in specific patients, dosage forms and administration modes. The dose level must be determined according to the activity of specific compound, administration route, severity of disease to be treated, and conditions and past medical history of patients. However, a conventional method in the art is to increase gradually the dose of compound from a level lower than that for achieving desired therapeutical effects to a level enough to achieve the desired therapeutical effects.

In the aforementioned or other treatment and/or prophylaxis, a compound of the present invention in a therapeutically and/or prophylactically effective amount can be used in form of pure compound, or in form of pharmaceutically acceptable esters or predrugs thereof (if they exist). Alternatively, the compound can be administered via a pharmaceutical composition comprising the compound and one or more pharmaceutically acceptable excipients. The term a compound of the present invention in a "therapeutically and/or prophylactically effective amount" means that the compound is in an amount sufficient to achieve prophylactically and/or therapeutically reasonal ratio of effect/risk. It should be understood that the total amount per day of the compound or composition of the present invention must be determined by a physician within the range of reliable medical decisions. As for any specific patients, the specific therapeutically amount must be determined based on various factors, including the diseases to be treated and severity thereof, the activity of the used specific compound, the used specific composition, the age, body weight, general health status, gender and food of patient, the administration time and route and excretory rate of the used specific compound, the drug(s) administered in combination or simultaneously with the specific compound, and similar factors well known in the art of medicine. For example, it is a common method in the art to increase gradually the dose of compound from a level lower than that for achieving desired therapeutical effects to a level enough to achieve the desired therapeutical effects. In general, the dose of a compound of formula I for mammals especially a human can be 0.001-1000 mg/kg body weight per day, such as 0.01-100 mg/kg body weight per day, 0.01-10 mg/kg body weight per day.

The compound according to the present invention can be used for effective prophylaxis and/or treatment of various diseases and disorders as mentioned in the present invention.

CONCRETE MODES FOR CARRYING OUT THE INVENTION

Examples

Figure 1:
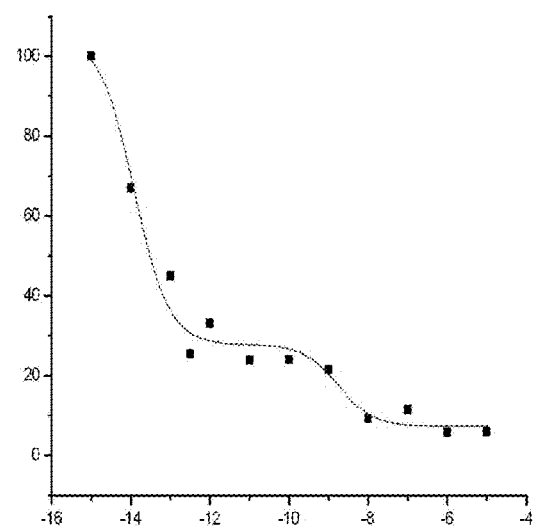
FIG. 1 is a competition-combination curve of Compound 1 of examples to D3R radioligand.

The present invention is further illustrated by the following examples, but these examples are not intended to restrict the present invention.

Example 1

Preparation of N-{4-[4-(5-chloro-2-methylphenyl) piperazinyl]butyl}-benzoxazolin-2-one-5-carboxamide (Compound 1, also called as Y-QA14)

(1) Benzoxazolin-2-one-5-carboxylic acid: 7.8 g (0.05 mol) of 3-amino-4-hydroxybenzoic acid was weighed, and added under stirring to 45 mL aqueous solution in which 8.5 g (0.08 mol) of anhydrous sodium carbonate was dissolved. The mixture was heated in a 45° C. oil bath, and added dropwise with 7.1 g of methyl chloroformate. After the addition, the reaction was carried out under stirring for 0.5 h, and then the temperature was elevated to 80° C. to keep the reaction overnight. In the next day, an acidification was carried out under cooling in an ice-water bath to pH 2-3, and a solid was filtered out, washed with a small amount of cold water, and dried to obtain a light brown powdery solid 7.5 g (83.3%), mp: 329-331° C. $^1$H-NMR (ppm, $d_6$-DMSO) δ: 7.385 (d, 1H, J=8.40 Hz, 7-H), 7.566 (d, 1H, J=1.68 Hz, 4-H), 7.74 (dd, 1H, J1=8.40 Hz, J2=1.68 Hz, 6-H), 11.868 (br-s, 1H, NH), 13.006 (br-s, 1H, CO2H).

(2) Benzoxazolin-2-one-5-carbonyl chloride: 0.5 g (2.80 mmol) benzoxazolin-2-one-5-carboxylic acid was weighed, dissolved in 30 ml 1,2-dichloroethane, and added dropwise with 0.67 g (5.6 mmol) thionyl chloride at room temperature. After addition, 10 drops of N,N-dimethylformamide was added as catalyst, and the reaction was heated to about 100° C. and carried out under reflux with stirring for 3 h, subjected to recovering solvent, transferred and dissolved in 15 ml anhydrous acetone for instant use.

(3) N-(4-bromobutyl)phthalimide: 93.6 g (0.43 mol) 1,4-dibromobutane was weighed, and added to 380 mL acetone. The mixture was added with 72.5 g (0.39 mol) phthalimide potassium salt and 2.1 g tetrabutylammonium iodide under stirring, subjected to refluxing for 18 h, cooled, filtrated to remove solid, and washed with acetone. All acetone solutions are combined, subjected to recovering the solvent under a reduced pressure, and added with petroleum ether for crystallization while the reaction mixture was hot. A solid was filtered out, washed with petroleum ether and dried to obtain a product 48.0 g (43.6%), mp 75~78° C. The mother liquor was concentrated to precipitate crystal, cooled in an ice-bath to obtain a solid 5.5 g (5.0%), mp 73~76° C.

(4) N-{4-[4-(5-chloro-2-methylphenyl)piperazinyl]butyl}phthalimide: N-(4-bromobutyl)phthalimide 7.0 g (0.025 mol) was weighed, and dissolved in 30 ml acetonitrile. The mixture was added with 4.2 g (0.02 mol) 5-chloro-2-methylphenyl-piperazine and dissolved under stirring, added dropwise with 5.05 g (0.05 mol) triethylamine after addition, heated to refluxing and reacted for 16 h. The reaction was subjected to recovering solvent under a reduced pressure after the end of reaction, washed with water, and extracted with ethyl acetate for 3 times. All organic layers were combined, dried with anhydrous sodium sulfate overnight, and subjected to recovering solvent to obtain a white viscous product, salified with hydrochloric acid ether to obtain a white solid product 7.55 g (78.0%), mp: 280-282° C. $^1$H-NMR (ppm, CDCl$_3$) δ: 1.60 (br-s, 2H), 1.76 (m, 2H), 2.23 (s, 3H), 2.45-2.60 (m, 4H), 2.88-2.96 (m, 6H), 3.75 (t, J=6.72 Hz, 2H), 6.95 (d, J=8.12 Hz, 2H), 7.08 (d, J=7.85 Hz, 1H), 7.72 (q, J=3.08 Hz, 2H), 7.84 (q, J=3.37 Hz, 2H).

(5) 4-[4-(5-chloro-2-methylphenyl)piperazinyl]-butylamine: N-{4-[4-(5-chloro-2-methylphenyl)piperazinyl]butyl}phthalimide hydrochloride 7.50 g (0.015 mol) was dissolved in 60 ml anhydrous ethanol. The mixture was added with 1.82 g (0.030 mol) hydrazine hydrate solution (content: 85%), heated to about 70° C., reacted under reflux with stirring for 4 h. After the completion of the reaction, ethanol was recovered under a reduced pressure, and the residual solid product was added with 15 ml 40% potassium hydroxide solution under stirring to dissolve. The solution was diluted with 30 mL water, and extracted with ethyl acetate for 3 times. All organic layers were combined, dried with anhydrous sodium sulfate overnight, and subjected to recovering solvent to obtain a light yellow oily product 3.83 g (88.2%). $^1$H-NMR (ppm, CDCl$_3$) δ: 1.56 (br-m, 4H), 2.24 (s, 3H), 2.42 (t, J=7.01 Hz, 2H), 2.60 (br-s, 4H), 2.76 (t, J=6.72 Hz, 2H), 2.92 (t, J=4.48 Hz, 4H), 6.94 (m, 2H), 7.06 (d, J=8.12 Hz, 1H).

(6) N-{4-[4-(5-chloro-2-methylphenyl)piperazinyl]butyl}-benzoxazolin-2-one-5-carboxamide: 0.73 g (2.60 mmol) 4-[4-(5-chloro-2-methylphenyl)piperazinyl]-butylamine was weighed, and added under stirring to 30 mL acetone solution in which 1.1 g (7.8 mmol) anhydrous potassium carbonate was dissolved. The mixture was added with the solution of benzoxazolin-2-one-5-carbonyl chloride (expressed as 2.80 mmol) as freshly prepared in step (2) in acetone, stirred at room temperature overnight, filtered under a reduced pressure in the next day, and washed sufficiently with acetone. The filtrates were collected, subjected to recovering acetone, washed with water, and extracted with dichloromethane for 3 times. All organic layers were combined, dried with anhydrous sodium sulfate, subjected to recovering dichloromethane, purified by column chromatography, and salified with hydrochloric acid ethyl ether to obtain a white solid product 0.89 g (78.1%), mp: 329-331° C. $^1$H-NMR δ (ppm, d$_6$-DMSO): 1.59 (br-s, 2H), 1.77 (br-s, 2H), 2.23 (s, 3H), 3.15 (br-m, 4H), 3.24 (br-m, 4H), 3.39 (q, J=7.00 Hz, 2H), 3.53 (d, J=12.05 Hz, 2H), 7.06 (m, 2), 7.23 (d, J=8.12 Hz, 1H), 7.37 (d, J=8.40 Hz, 1H), 7.58 (d, J=1.68 Hz, 1H), 7.67 (dd, J$_1$=8.40 Hz, J$_2$=1.68 Hz, 1H), 8.62 (br-s, 1H, NH), 10.57 (br-s, 1H, CO$_2$H). MS (ESI$^+$, m/z): 443.2/445.3 (M+H$^+$, 3:1).

Example 2

Preparation of N-{4-[4-(5-chloro-2-methylphenyl)piperazinyl]-butyl}-benzoxazolin-2-one-6-carboxamide (Compound 2)

(1) Benzoxazolin-2-one-6-carboxylic acid: according to the method of Example 1, 4-amino-3-hydroxybenzoic acid and methyl chloroformate were heated for cyclization in the presence of sodium carbonate as deacidificating agent. The yield was 84.6%, mp: 312-316° C. $^1$H-NMR (ppm, d$_6$-DMSO) δ: 7.19 (d, 1H, J=8.12 Hz, 4-H), 7.74 (s, 1H, 7-H), 7.81 (dd, 1H, J$_1$=8.12 Hz, J$_2$=0.84 Hz, 5-H), 12.07 (br-s, 1H, NH), 12.85 (br-s, 1H, CO$_2$H).

(2) Preparation of N-{4-[4-(5-chloro-2-methylphenyl)-piperazinyl]butyl}-benzoxazolin-2-one-6-carboxamide: according to the method of Example 1, benzoxazolin-2-one-6-carboxylic acid was used to prepare benzoxazolin-2-one-6-carbonyl chloride, which then was reacted with 4-[4-(5-chloro-2-methylphenyl)piperazinyl]butylamine, and subjected to acylation in the presence of sodium carbonate as deacidficating agent to provide the product. The yield was 81.2%, mp: 205-209° C. $^1$H-NMR (ppm, CDCl$_3$) δ: 1.57-1.59 (s, br., 2H), 1.74 (s, br., 2H), 2.23 (s, 3H), 3.01 (m, 2H), 3.18 (br, 4H), 3.38 (br, 4H), 3.54 (d, J=10.92 Hz, 2H), 7.06 (m, 2H), 7.15 (d, J=8.2 Hz, 1H), 7.72-7.77 (m, 2H), 8.55 (s, 1H).

Example 3

Preparation of N-{4-[4-(2-methyloxyphenyl)piperazinyl]butyl}-benzoxazolin-2-one-5-carboxamide (Compound 3)

(1) 4-[4-(2-methyloxyphenyl)piperazinyl]butylamine: according to the method of claim 1, N-(4-bromobutyl)phthalimide and 2-methyloxyphenyl-piperazine was used in reaction to produce N-{4-[4-(2-methyloxyphenyl)piperazinyl]butyl}phthalimide, which was then reacted with hydrazine hydrate. The yield was: 84.3%. Hydrochloride salt had a mp: 173-175° C.

(2) N-{4-[4-(2-methyloxyphenyl)piperazinyl]butyl}-benzoxazolin-2-one-5-carboxamide: according to the method of Example 1, benzoxazolin-2-one-5-carbonyl chloride and 4-[4-(2-methyloxyphenyl)piperazinyl]butylamine were subjected to acylation in the presence of sodium carbonate as deacidficating agent to provide the product. Yield: 79.2%, mp: 208-212° C. $^1$HNMR (ppm, CDCl$_3$) δ: 1.53 (m, 4H), 2.36 (m, 2H), 2.94 (s, br., 4H), 3.27 (m., 2H), 3.35 (m, 4H), 3.76 (s, 3H), 6.85 (m, 2H), 6.94 (m, 2H), 7.34 (d, J=8.4 Hz, 1H), 7.55 (d, J=1.4 Hz, 1H), 7.55 (dd, J$_1$=1.4 Hz, J$_2$=8.4 Hz, 2H), 8.51 (t, J=5.6 Hz, 1H).

Example 4

Preparation of N-{4-[4-(2-methyloxyphenyl)piperazinyl]butyl}-benzoxazolin-2-one-6-carboxamide (Compound 4)

According to the method of Example 3, 4-[4-(2-methyloxyphenyl)piperazinyl]butylamine and benzoxazolin-2-one-6-carbonyl chloride were subjected to acylation in the presence of sodium carbonate as deacidficating agent to obtain the product. Yield: 71.2%. mp: 175-177° C. $^1$HNMR (ppm, DMSO-d$_6$) δ: 1.53 (m, 4H), 2.36 (m, 2H), 2.50 (s, br., 4H), 2.94 (s, br., 4H), 3.28 (m, 2H), 3.76 (s, 3H), 6.86 (m, 2H), 6.93 (m, 2H), 7.15 (d, J=8.1 Hz, 1H), 7.70-7.74 (m, 2H), 8.42 (t, J=5.6 Hz, 1H).

Example 5

Preparation of N-{4-[4-(5-chloro-2-methylphenyl)piperazinyl]-trans-2-butyl}-benzoxazolin-2-one-6-carboxamide (Compound 5)

(1) Trans-4-[4-(5-chloro-2-methylphenyl)piperazinyl]-2-buten-1-amine: according to the method of Example 1, phthalimide potassium salt was reacted with trans-1,4-dihydro-2-butene to obtain N-(trans-4-chloro-2-buten-1-yl)phthalimide, mp: 108-110° C.; which was then reacted with 5-chloro-2-methylphenylpiperazine to obtain N-{4-[4-(5-chloro-2-methylphenyl)piperazinyl]-trans-2-buten-1-yl}phthalimide, which was then reacted with hydrazine hydrate to obtain the product. Yield: 89.3%. Hydrochloride mp: 140-142° C. $^1$HNMR (ppm, CDCl$_3$) δ: 1.46 (br-s, 4H), 2.25 (s, 3H), 2.61 (br-s, 2H, NH$_2$), 2.93 (m, 4H), 3.10 (d, J=7.0 Hz), 3.39 (d, J=6.72 Hz, 2H), 5.58 (m, 1H), 5.71 (m, 1H), 6.96 (m, 2H), 7.06 (d, J=7.84, 1H).

(2) N-{4-[4-(5-chloro-2-methylphenyl)piperazinyl]-trans-2-buten-1-yl}-benzoxazolin-2-one-6-carboxamide: according to Example 2, benzoxazolin-2-one-6-carbonyl chloride and trans-4-[4-(5-chloro-2-methylphenyl)piperazinyl]-2-buten-1-amine were subjected to acylation in the presence of sodium carbonate as deacidficating agent to provide the product. Yield: 88.6%, mp: 250-252° C. $^1$HNMR δ (ppm, DMSO-d$_6$): 2.19 (s, 3H), 2.83 (br-s, 4H), 3.31 (s, br., 2H), 3.88 (s, br., 4H), 3.91 (d, J=1.15 Hz, 2H), 5.67 (m, 2H), 6.97 (t, J=1.96 Hz, 2H), 7.16 (q, J=4.48 Hz, 2H), 7.75 (m, 2H), 8.63 (br-s, 1H).

Example 6

Preparation of N-{4-[4-(5-chloro-2-methylphenyl)piperazinyl]-cis-2-buten-1-yl}-benzoxazolin-2-one-5-carboxamide (Compound 6)

(1) Cis-4-[4-(5-chloro-2-methylphenyl)piperazinyl]-2-buten-1-amine: according to the method of Example 5, phthalimide potassium salt was reacted with cis-1,4-dihydro-2-butene to obtain N-(cis-4-chloro-2-buten-1-yl)phthalimide; which was then reacted with 5-chloro-2-methylphenylpiperazine to obtain N-{4-[4-(5-chloro-2-methylphenyl)piperazinyl]-cis-2-buten-1-yl}phthalimide, which was then reacted with hydrazine hydrate. Yield: 85.7%. Hydrochloride mp: 127-129° C. $^1$HNMR (ppm, CDCl$_3$) δ: 1.56 (br-s, 4H), 2.23 (s, 3H), 2.71 (br-s, 2H, NH$_2$), 2.96 (m, 4H), 3.12 (d, J=7.0 Hz), 3.41 (d, J=6.72 Hz, 2H), 5.60 (m, 1H), 5.73 (m, 1H), 6.96 (m, 2H), 7.08 (d, J=7.84, 1H).

(2) N-{4-[4-(5-chloro-2-methylphenyl)piperazinyl]-cis-2-butyl}-benzoxazolin-2-one-5-carboxamide: according to the method of Example 5, benzoxazolin-2-one-5-carbonyl chloride and cis-4-[4-(5-chloro-2-methylphenyl)piperazinyl]-2-butenyl-1-amine were subjected to acylation in the presence of sodium carbonate as deacidficating agent to obtain the product. Yield: 86.3%, mp: 251-253° C. $^1$H-NMR (ppm, CDCl$_3$) δ: 2.20 (s, 3H), 2.49 (m, 4H), 2.84 (br-s, 4H), 3.12 (d, J=6.44 Hz), 3.97 (t, J=5.60, 2H), 5.62 (m, 2H), 6.99 (m, 2H), 7.17 (d, J=9.1 Hz, 1H), 7.36 (d, J=8.4 Hz 1H), 7.66 (m, 2H).

Example 7

Preparation of N-{4-[4-(2-methyloxyphenyl)piperazinyl]-trans-2-buten-1-yl}-benzoxazolin-2-one-5-carboxamide (Compound 7)

(1) Trans-4-[4-(2-methyloxyphenyl)piperazinyl]-2-buten-1-yl-amine: according to the method of Example 5, N-(trans-4-chloro-2-buten-1-yl)phthalimide was reacted with 1-(2-methyloxyphenyl)piperazine to obtain N-{4-[4-(2-methyloxy-phenyl)piperazinyl]-trans-2-buten-1-yl}phthalimide, which was then reacted with hydrazine hydrate. Yield: 85.6%, hydrochloride mp: 178-180° C.

(2) N-{4-[4-(2-methyloxyphenyl)piperazinyl]-trans-2-buten-1-yl}-benzoxazolin-2-one-5-carboxamide: according to the method of Example 1, benzoxazolin-2-one-5-carbonyl chloride and trans-4-[4-(2-methyloxyphenyl)piperazinyl]-2-buten-1-amine were subjected to acylation in the presence of sodium carbonate as deacidficating agent to provide the product. Yield: 85.6%, mp: 208-212° C. $^1$H-NMR (ppm, DMSO-d$_6$) δ: 2.99 (m, 4H), 3.09 (m, 2H), 3.78 (s, br., 4H), 3.79 (s, 3H), 3.96 (t, J=5.6 Hz, 2H), 5.73 (m, 1H), 6.02 (m, 1H), 6.92 (m, 2H), 6.98 (m, 2H), 7.36 (d, J=8.4 Hz, 1H), 7.58 (d, J=1.4 Hz, 1H), 7.66 (dd, J$_j$=1.4 Hz, J$_2$=8.4 Hz, 2H), 8.81 (t, J=5.5 Hz, 1H).

Example 8

Preparation of N-{4-[4-(2-methyloxyphenyl)piperazinyl]-trans-2-buten-1-yl}-benzoxazolin-2-one-6-carboxamide (Compound 8)

According to the method of Example 7, trans-4-[4-(2-methyloxyphenyl)piperazinyl]-2-buten-1-yl-amine and benzoxazolin-2-one-6-carbonyl chloride were subjected to acylation in the presence of sodium carbonate to obtain the product. Yield: 87.5%. mp: 200-202° C. $^1$HNMR (ppm, DMSO-d$_6$) δ: 2.50 (m, 4H), 2.96 (s, br., 4H), 3.31 (m, 2H), 3.75 (s, 3H), 3.89 (t, 2H), 5.62-5.67 (m, 2H), 6.86 (m, 2H), 6.91 (m, 2H), 7.14 (d, J=8.2 Hz, 1H), 7.73-7.77 (m, 2H), 8.63 (t, J=5.6 Hz, 1H).

Example 9

Preparation of N-{4-[4-(2-methyloxyphenyl)piperazinyl]butyl}-benzothiazolin-2-one-6-carboxamide (Compound 9)

(1) 4-amino-3-thiocyano-benzonitrile: 10.0 g (0.08 mol) p-aminobenzonitrile, 13.0 g (0.17 mol) ammonium thiocyanate were dissolved in 100 ml glacial acetic acid, added dropwise with a glacial acetic acid solution in which 4 mL was dissolved under cooling in an ice-water bath. After the addition, the reaction was performed under stirring for 3 h, and continued at room temperature for 30 min. After the end of reaction, the reaction mixture was added with water to promote precipitation, stood overnight, filtered to collect the precipitate, washed with a small amount of water, dried out to obtain an orange-yellow solid product 13.2 g (89.7%). mp 168-170° C. $^1$H-NMR δ (ppm, d$_6$-DMSO): 6.68 (d, J=8.68 Hz, 1H), 6.96 (br-s, 2H, NH$_2$), 7.58 (dd, J$_1$=8.70 Hz, J$_2$=1.68 Hz, 1H), 7.96 (d, J=1.60 Hz, 1H).

(2) 2-amino-benzo[d]thiazole-6-carboxylic acid: 13.0 g (0.07 mol) 4-amino-3-thiocyano-benzonitrile was weighed, dissolved in 120 ml water, stirred uniformly, added with 60 ml concentrated hydrochloric acid, reacted under refluxing and stirring at about 100° C. for 6 h. After the reaction, the reaction mixture was stood, filtered to obtain a precipitated solid, and dried out to obtain a light yellow solid product 8.5 g (59.0%). mp 280-282° C. ¹H-NMR (ppm, d₆-DMSO) δ: 7.45 (d, J=8.40 Hz, 1H), 7.67 (dd, J₁=8.40 Hz, J₂=1.68 Hz, 1H), 8.22 (d, J=1.68 Hz, 1H), 8.51 (br-s, 2H, NH₂).

(3) 4-amino-3-thio-benzoic acid: 25.0 g potassium hydroxide was weighed, dissolved in 50 ml water, slightly cooled, added with 8.3 g (0.04 mol) 2-amino-benzo[d]thiazole-6-formic acid under nitrogen gas protection, reacted under refluxing and stirring for 24 h, after the end of reaction, cooled with ice bath, added with hydrochloric acid for acidification, stood and filtered to obtain a white solid product 5.2 g (67.9%). mp 280-284° C. ¹H-NMR δ (ppm, d₆-DMSO): 6.75 (d, J=8.69 Hz, 1H), 7.46 (d, J=1.96 Hz, 1H), 7.63 (dd, J₁=1.96 Hz, J₂=8.40 Hz, 1H), 12.13 (br-s, 1H, CO₂H).

(4) benzothiazolin-2-one-6-carboxylic acid: 5.0 g (0.03 mol) 4-amino-3-mercapto-benzoic acid was weighed, added under stirring to 40 mL aqueous solution in which 5.3 g (0.05 mol) anhydrous sodium carbonate was dissolved, under protection of nitrogen gas, heated in 45° C. oil bath, added dropwise with 4.3 g (0.04 mol) methyl chloroformate, after addition, reacted under stirring for 0.5 h, then heated to 80° C. for reaction overnight. On the next day, acidification was carried out under ice-water to pH2~3, a solid was obtained by filtration, washed with a small amount of cold water, dried to obtain a white powdery solid 4.8 g (82.2%), mp 322-328° C. ¹H-NMR δ (ppm, d₆-DMSO): 7.1 (d, J=8.40 Hz, 1H), 7.8 (dd, J₁=8.40 Hz, J₂=1.68 Hz, 1H), 8.18 (d, J=1.68 Hz, 1H), 12.25 (br-s, 1H, NH), 12.89 (br-s, 1H, CO₂H). MS (ESI⁻, m/z): 194.2 (M-1).

(5) N-{4-[4-(2-methyloxyphenyl)piperazinyl]butyl}-benzothiazolin-2-one-6-carboxamide: according to the method of Example 3, benzothiazolin-2-one-6-carboxylic acid was used to prepare benzothiazolin-2-one-6-carbonyl chloride, which was then reacted with 4-[4-(2-methyloxyphenyl)piperazinyl]butylamine, and acylated in the presence of sodium carbonate as deacidificating agent. Yield: 81.0%. mp: 154-159° C. ¹H-NMR (ppm, CDCl₃) δ: 1.58 (m, 4H), 1.72 (m, 2H), 2.79 (br., 4H), 3.11 (br., 4H), 3.49 (m, 2H), 3.85 (s, 3H), 6.86 (m, 2H), 6.98 (m, 2H), 7.08 (d, J=8.4 Hz, 1H), 7.62 (dd, J₁=1.7 Hz, J₂=8.4 Hz, 1H), 7.83 (d, J=1.7 Hz, 1H).

Example 10

Preparation of N-{4-[4-(5-chloro-2-methylphenyl)piperazinyl]-butyl}-benzothiazolin-2-one-6-carboxamide (Compound 10)

According to the method of Example 1, 4-[4-(5-chloro-2-methylphenyl)piperazinyl]butylamine and benzothiazolin-2-one-6-carbonyl chloride were subjected to acylation in the presence of sodium carbonate as deacidificating agent to obtain a product. Yield: 79.6%. mp: 216-220° C. ¹H-NMR (ppm, DMSO-d₆) δ: 1.51 (m, 2H), 1.73 (m, 2H), 2.04 (s, 3H), 2.19 (s, br., 4H), 3.13 (br, 4H), 3.35 (m, 2H), 7.13 (m, 2H), 7.15 (m, 2H), 7.17 (d, J=8.2 Hz, 1H), 7.76 (dd, J₁=1.7 Hz, J₂=8.2 Hz, 1H), 8.05 (d, J=1.7 Hz, 1H).

Example 11

Preparation of N-{4-[4-(2-methyloxyphenyl)piperazinyl]-trans-2-buten-1-yl}-benzothiazolin-2-one-6-carboxamide (Compound 11)

According to the method of Example 7, trans-4-[4-(2-methyloxyphenyl)piperazinyl]-2-butenylamine reacted with benzoxazolin-2-one-6-carbonyl chloride for acylation in the presence of sodium carbonate to obtain a product. Yield: 80.7%. mp: 160-164° C. ¹H-NMR (CDCl₃) δ: 2.76 (s, br., 4H), 3.13 (s, br., 6H), 3.85 (s, 3H), 4.08 (t, J=5.3 Hz, 2H), 5.79 (m, 2H), 6.84 (m, 2H), 6.90 (m, 2H), 7.05 (d, J=8.2 Hz, 1H), 7.63 (dd, J₁=1.7 Hz, J₂=8.2 Hz, 1H), 7.78 (d, J=1.7 Hz, 1H).

Example 12

Preparation of N-{4-[4-(2-methyloxyphenyl)piperazinyl]butyl}-benzothiazolin-2-one-5-carboxamide (Compound 12)

(1) 3-amino-4-mercaptobenzoic acid: 100 g (0.53 mol) 4-chloro-3-nitrobenzoic acid was suspended in 400 mL water, added as one batch to 300 mL aqueous solution in which 300 g (1.25 mol) sodium sulfide was dissolved, the reaction liquid reacted under stirring and refluxing for 7 h, cooled, neutralized with acetic acid to pH7.5, decolorized with active carbon, filtered, acidificated with acetic acid again to pH4.5, a solid was obtained by filtration, washed with water, crystallized with methanol-water to obtain a yellow solid 62.5 g (62.5%), mp: 185° C. (dec.).

(2) benzothiazolin-2-one-5-carboxylic acid: it was synthesized by referring to the process for preparing benzothiazolin-2-one-6-carboxylic acid, yield 78.5%, mp: >320° C.

(3) N-{4-[4-(2-methyloxyphenyl)piperazinyl]butyl}-benzothiazolin-2-one-5-carboxamide: 4-[4-(2-methyloxyphenyl)piperazinyl]butylamine 2.70 g (0.010 mol) was dissolved in 60 mL dichloromethane, added under stirring with 2.00 g (0.010 mol) benzothiazolin-2-one-6-carboxylic acid, added with supplementary 15 mL acetone, then added with 1.38 g (0.010 mol) 1-hydroxy-benzotriazole and 2.25 g (0.011 mol) N,N'-dicyclohexylcarbodiimide, added with supplementary 3 mL anhydrous methanol, reacted under stirring overnight. On the next day, the reaction mixture was filtered to remove solid, washed with dichloromethane, organic layers were combined, added with supplementary 4 mL ethanol, added with water, layered, dried, subjected to silica gel column chromatography to obtain a fraction with maximum polarity, concentrated to obtain a viscous product, which was salified with hydrochloric acid-ethyl ether to obtain the target product 3.50 g (73.4%), mp: 135-138° C. ¹H-NMR (CDCl₃) δ: 1.81 (m→br, 2H), 2.05 (m→br, 2H), 3.25 (m→br, 2H), 3.49-3.74 (m, 6H), 4.031 (s, 3H), 4.20 (m→br, 2H), 4.77 (m→br, 2H), 7.044 (d, J=8.12 Hz, 2H), 7.172 (s, 1H), 7.41 (m, 2H), 7.50 (m→br, 1H), 7.604 (d, J=7.00 Hz), 7.977 (br-s, 1H), 8.511 (s, 1H), 12.914 (br-s, 1H).

Example 13

Preparation of N-{4-[4-(5-chloro-2-methylphenyl)piperazinyl]-butyl}-benzothiazolin-2-one-5-carboxamide (Compound 13)

According to the method of Example 12, 4-[4-(5-chloro-2-methylphenyl)piperazinyl]butylamine was used to replace 4-[4-(2-methyloxyphenyl)piperazinyl]butylamine in the synthesis, yield 78.5%, mp: 130-133° C. ¹H-NMR (ppm, DMSO-d₆) δ: 1.59 (m, 2H), 1.78 (m, 2H), 2.231 (s, 3H), 3.10-3.25 (m, 8H), 3.12 (m, 2H), 3.53 (m, 2H), 4.819 (br, 2H), 7.04 (d, J=1.96 Hz, 1H), 7.07 (dd, J₁=1.96 Hz, J₂=8.12 Hz, 1H), 7.22 (d, J=8.12 Hz, 1H), 7.606 (s, 1H), 7.665 (s, 2H), 8.675 (t, J=5.32 Hz, 1H), 10.838 (br-s, 1H), 12.187 (s, 1H).

The present invention is further illustrated by the following biological activity experiments.

Biological Effect Experiment 1

Experiment of Binding a Target Compound to Radioligands of Dopamine D3 and D2 Receptor (D2R)

Experimental materials: stably transfected CHO-D3R cell strains and CHO-D2R cell strains, $^3$H-Spiperone, purchased from GE Company, Haloperidol, Quinpirole, purchased from Sigma Company, $^{35}$S-GTPγS purchased from PE Company, GTP-γS, GDP, Tris, EDTA-Na$_2$, EGTA, HEPES, PMSF, PPO and POPOP purchased from Sigma Company, NaCl, KCl, KH$_2$PO$_4$, CaCl$_2$, Glucose, MgSO$_4$, MgCl$_2$ and CaCl$_2$, analytically pure, purchased from Beijing Chemical Reagent Company, dioxane, naphthalene and ethylene glycol, purchased from Beijing Chemical Reagent Company, GF/C filter paper purchase from Whatman Company, the compounds were obtained by the above methods.

Experimental steps: the compounds were weighed separately, when cells reached fusion degree of 90%, the cells were digested, centrifuged at 4° C. under 2000 rpm for 5 min. Supernatant was discarded, and precipitation was performed in 5 mM Tris, 5 mM EDTA.2Na and 5 mM EGTA lysate (pH 7.4), stood on ice for 30 min, subjected to passing through syringe needle (4# needle, 0.45×13 mm disposable syringe) under ice-bast for 5-10 times, 4° C., and centrifuged under 40000 g for 20 min. Supernatant was discarded, precipitate was suspended again in ice-cooled 50 mM Tris-HCl (pH 7.4) buffer solution, subjected to passing through needle for 5-10 times, and centrifuged under 4° C., 40000 g for 20 min. Protein concentration was measured by Coomassie brilliant blue G-250 method. Ice-bath was used for adding to reaction system. The used reaction buffer solution was 50 mM Tris-HCl (pH 7.4) buffer solution comprising 1.5 mM CaCl$_2$, 4 mM MgCl$_2$, 1 mM EDTA, 5 mM KCl and 120 mM NaCl. Radioligand $^3$H-Spiperone with a concentration of 0.15-4.8 nM, membrane protein 25-30 μg/tube were used; non-specific binding tube further comprised Haloperidol 10 μM, various other compounds had a final concentration of 1 μM or 50 nM, the total reaction volume was 0.2 mL, the reaction was carried out under 25° C. water bath for 60 min, filtered under a reduced pressure, loaded with scintillation fluid 1 mL, cpm was measured after a night. The results were shown in Table 1 and Table 2.

TABLE 1

Comparative results of selectivity screening of the target compounds at a concentration of $10^{-6}$ M on D3R and D2R

| No. | D2R inhibition percentage (%) | D3R inhibition percentage (%) |
|---|---|---|
| NGB2904 | 7.67 ± 9 | 85.88 ± 11 |
| Compound 1 | 56.97 ± 17 | 91.00 ± 11 |
| Compound 6 | 63.60 ± 1 | 68.43 ± 4 |

TABLE 2

Comparative results of affinity and selectivity screening of the target compounds at a concentration of 50 nM on D3R and D2R

| No. | D3R inhibition (%) | D2R inhibition (%) |
|---|---|---|
| NGB2904 | 51.8 ± 6 | 3.87 ± 3 |
| Compound 1 | 67.07 ± 12 | 3.9 ± 3.4 |
| Compound 2 | 86 | 5 |
| Compound 5 | 72 | 0 |
| Compound 6 | 24.4 ± 6 | 2.1 ± 10 |

The compounds of other examples of the present invention also had similar experimental results as the example compounds of the present invention in Table 1 and Table 2.

Biological Effect Experiment 2

Experiment of Competitive Inhibition Constant Ki for Compound 1 (Y-QA14) to D3R and D2R The experimental method and steps were identical to those of the biological effect experiment 1, the tested compound Y-QA14 had concentrations from $10^{-16}$ to $10^{-5}$M, increasing by 10 times from $10^{-16}$M, including 12 concentrations for the experiment, the obtained data were treated with competitive inhibition curve analysis of OriginPro 7.0 software to calculate $K_i$ values.

Figure 2:
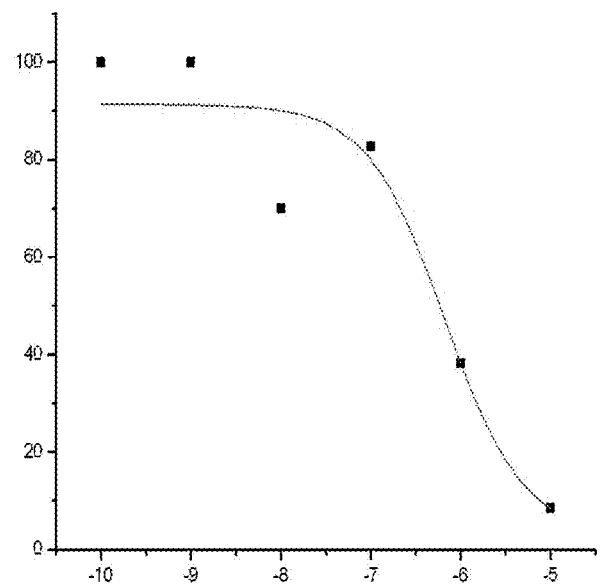
FIG. 2 is a competition-combination curve of Compound 1 of examples to D2R radioligand.

The results were shown in FIG. 1 and FIG. 2. The results indicate that Compound 1 (Y-QA14) has two binding sites at D3R, their Ki values separately are $Ki_H$=0.052±0.003 pM, $Ki_L$=2.03±0.4 nM; while Compound 1 has only one binding site at D2R, Ki is 134.5±10.2 nM. By comparison, it can be seen that Compound 1 has a selectivity of $10^6$ and 66 times respectively to D3R and D2R, and its value to the high affinity binding site is higher than the D3R compound with high selective in the art by about 1000 times.

Biological Effect Experiment 3

Studying on Intrinsic Activity of Compound 1 (Y-QA14)

Figure 3:
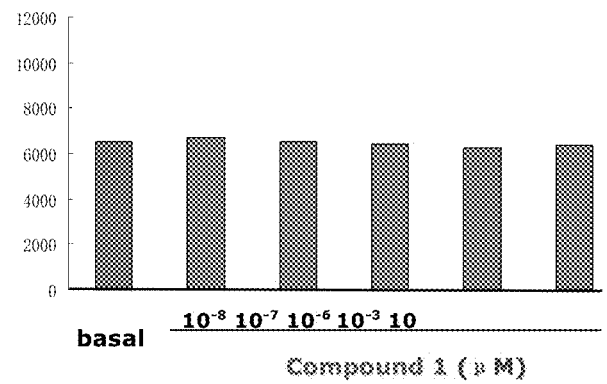
FIG. 3 is a diagram showing the effects of Compound 1 of examples on activity of $^{35}$S-GTPγS binding D3R, in which "basal" represents basis.
Figure 4:
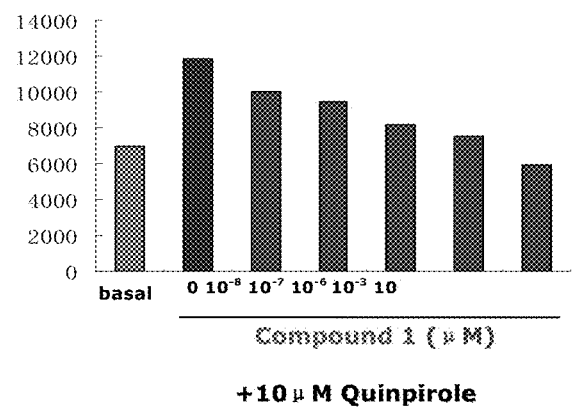
FIG. 4 is a diagram showing the effects of Compound 1 of examples on activity of quinpirole activated $^{35}$S-GTPγS binding D3R, in which "basal" represents basis.

Experimental method: Membrane protein was added to the reaction system under ice-water bath. The reaction buffer was 50 mM Tris-HCl (pH 7.4) buffer, comprising 3 mM MgCl$_2$, 100 mM NaCl and 10 μMGDP. Radioligand $^{35}$S-GTPγS was of 0.17 nM, membrane protein was 40-45 μg/tube; irritant drugs were pre-incubated with protein at 30° C. for 30 min (not adding $^{35}$S-GTPγS), then added with $^{35}$S-GTPγS and incubated at 30° C. for 30 min. Non-specific binding tube further comprised GTPγS 40 μM. The total reaction volume was 0.5 mL, the reaction was terminated with ice-water bath. The reaction liquid was filtrated under a reduced pressure by Whatman-GF/C filter paper, and washed 5 times with cold buffer solution 50 mM Tris-HCl (pH 7.4) containing 5 mM MgCl$_2$ and 50 mM NaCl. The filter paper was dried and placed in 1.5 mL Ep tubes, added with 1 mL scintillation fluid, placed in a scintillation disc, and β liquid scintillation counter was used to record intensity of radiation (cpm). Specific binding amount=total binding amount−non-specific binding amount, multiple tubes were used for each binding site. The data were analyzed by Logistic formula of OriginPro 7.0 software. The results are shown in FIG. 3 and FIG. 4. The results show that in the $^{35}$S-GTPγS binding experiment, single Y-QA14 cannot activate D3R coupling G protein, but it can inhibit the agitation activity of D3R agonist in a concentration dependent way.

Biological Effect Experiment 4

Influence of Compound 1 (Y-QA14) on Conditioned Place Preference Caused by Morphine in Rats Experimental mechanism: Conditioned Place Preference (CPP) experiment is a classical experimental model in the art currently used for evaluating psychological dependence of drug, in which test animals (rats, mice) are placed in the white viewing area of a conditioned place preference experimental box, administrated with morphine as psychological dependent drug, then the activities of animals in the black and white viewing areas of the conditioned place preference experimental box are observed, the animals are free to move through small doors among black area, white area and grey area. Every time when the animals are in the administration area, they are rewarded with drug to generate a place preference to black or white area, which degree relates to the psychological dependence of the drug.

Experimental materials: animal: wistar rats, male, body weight 180-220 g; reagent: morphine hydrochloride (Qinghai Pharmaceutical Factory); Compound Y-QA14 was synthesized by the inventors.

Instruments: Conditioned Place Preference Instrument for Rats

Preparation of Drugs:

Morphine: 10 mg/kg, dissolving 1 mg morphine in 1 mL double-distilled water;

Y-QA14: 1.0 mg/kg, dissolving 0.1 mg Y-QA14 in DMSO, then adding double-distilled water to reach 1 mL; 5.0 mg/kg, dissolving 0.5 mg Y-QA14 in DMSO, then adding double-distilled water to reach 1 mL; 10.0 mg/kg, dissolving 1 mg Y-QA14 in DMSO, then adding double-distilled water to reach 1 mL.

Experimental steps: comprising 3 stages: pre-test stage, training stage and test stage, and operating for consecutive 13 days for completion.

1) Pre-Test Session

In the 1st to 3rd day, the clapboards between two boxes was withdrawn, rats were placed in the middle box, the rats were allowed to run freely in 3 boxes for 15 min, the dwell time of animals in each of the two boxes was measured in order to determine the natural preference to black and white boxes. The box with shorter dwell time for animals was used as drug-box, the white box usually was the drug-box; while the one with longer dwell time was preference box, used as non-drug box.

2) Training Session

In the 4th to 12th day, the clapboards were inserted so that the animals could not move freely between boxes. The experiment was performed every day between 8:30 am and 14:30 am. The animals were trained with saline and drug separately once per day for consecutive 7 days. The animals of 3 Y-QA14 dose groups were abdominally administered with various doses of Y-QA14, after 20 min, subcutaneously injected with morphine 10 mg/kg and then placed immediately in the white box (drug box) for 45 min, or subcutaneously injected with saline and then placed immediately in the black box (non-drug box) for 45 min, circulated once per day. The animals of the solvent group were abdominally administered with saline, after 30 min, subcutaneously injected with solvent and then placed immediately in the white box, subcutaneously injected with saline and then placed immediately in the black box (non-drug box) for 45 min, circulated once per day.

3) Test Session

On the 13th day, the clapboards were withdrawn between two boxes, the mice were placed in the middle box, and allowed to run freely in the 3 boxes from 15 min, and the dwell time of the mice in the white box (drug box) was recorded by computer.

Five groups were used in the experiment: (1) solvent+physiological saline; (2) morphine+solvent; (3) morphine+Y-QA14 1.0 mg/kg; (4) morphine+Y-QA14 5.0 mg/kg; (5) morphine+Y-QA14 10.0 mg/kg.

Figure 5:
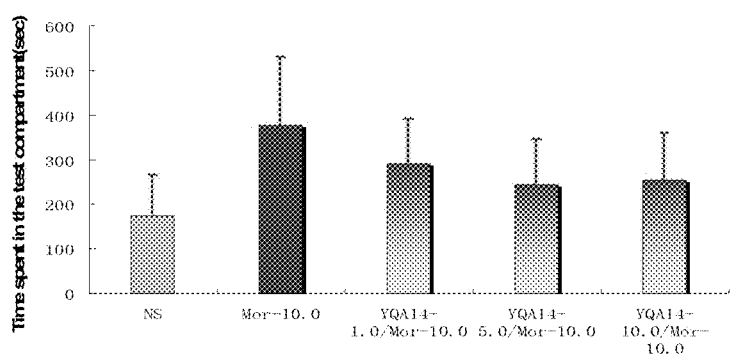
FIG. 5 is a diagram showing the effects Compound 1 (Y-QA14) of examples on the conditioned place preference caused by morphine in rats, in which as compared to the saline group, **$P<0.005$; as compared to the morphine group, #$P<0.02$; mean±SD; n=10; and "Time spent in the test compartment (sec)" of the ordinate represents the time (s) spending in the test interval zone.

Experimental results: the dwell times of mice of various groups in the drug box were compared; the data were statistically analyzed by single factor multi-level variance analysis. The results were shown in FIG. 5. The experimental results show that in the experiment of conditioned place preference caused by morphine in rats, Y-QA14 at two dose levels 5 mg/kg and 10 mg/kg can significantly inhibit the occurrence of conditioned place preference caused by morphine.

Biological Effect Experiment 5

Observation of Compound 1 (Y-QA14) Against Mental Diseases

Experimental object: two pharmacological experimental methods for representing center dopamine functions and behaviors were used, using typical antipsychotic drug haloperidol as reference, preliminarily discussing the possibility of using Y-QA14 as potential antipsychotic drug.

Experimental materials: animals: Kunming mice, male, body weight 20-30 g; reagents: amfetamine (SIGMA); apomorphine (SIGMA); haloperidol (the Institute of Toxicology and Pharmacology, the Academy of Military Medical Sciences); Compound Y-QA14 was synthesized by the inventors.

Preparation of Drugs: Amfetamine was Prepared with Distilled Water; apomorphine and haloperidol were prepared by dissolving in 0.5N hydrochloric acid and adding with 5% DMSO aqueous solution; Y-QA14 was dissolved in DMSO and diluted with water.

Experimental Method:

1) Apomorphine Mice Climbing Test

Mice were subcutaneously injected with apomorphine 2 mg/kg as dopamine agonist, placed in a metal wire cage, apparent climbing behavior occurred in the animals after 5 min, animals which climbed cage wall and suspended without limbs in contact with the ground for consecutive 20 s or more were positive animals, the action peak was reached after 15-30 min in the injected model animals. Antipsychotic drug haloperidol and Y-QA14 were intraperitoneally injected before 30 min of apomorphine administration. The climbing rates of positive animals measured after 15 min and 30 min of apomorphine administration in each group were recorded and compared, the higher one was used in calculation (see: Moore N A et al. J Clin Psychiatry 1997, 58 (Suppl 10): 37-44).

2) Test of Hyperactivity in Amfetamine Mice

Mice which was subcutaneously injected with 6 mg/kg amfetamine after 15 min showed an increase in spontaneous activity, and placed in an infrared spontaneous activity instrument (Institute of Materia Medica, Chinese Academy of Medical Sciences), each in one box, the activity number in 10 min was recorded. Antipsychotic drug and Y-QA14 were intraperitoneally injected before 15 min of amfetamine administration. The average spontaneous activity numbers of the groups were recorded and compared (see: Moore N A et al. J Clin Psychiatry 1997, 58 (Suppl 10): 37-44).

Experimental Results:

1) Apomorphine Mice Climbing Test

Apomorphine 2 mg/kg, sc caused 87% animals appearing climbing behavior, after being inhibited with haloperidol 0.1 mg/kg, only 25% animals appeared climbing behavior, after being inhibited with haloperidol 0.2 mg/kg, the animals appearing climbing behavior were further reduced to 12.5%. Intraperitoneal injection of Y-QA14 20 mg/kg did not show significant inhibition effect, 30 mg/kg showed partial inhibition, while 40 mg/kg showed significant inhibition, no animal appeared climbing behavior as shown in Table 3.

TABLE 3

Antagonistic effect of intraperitoneal injection of Y-QA14 on apomorphine mice climbing behaviors

| Drug | Dose (mg/kg) | Route | Animal Number | Climbing rate |
|---|---|---|---|---|
| Apomorphine control | 2 | sc | 8 | 7/8 |
| Haloperidol | 0.1 | ip | 8 | 2/8* |
|  | 0.2 | ip | 8 | 1/8** |
| Y-QA14 | 20 | ip | 8 | 8/8 |
|  | 30 | ip | 8 | 6/8 |
|  | 40 | ip | 8 | 0/8** |

Note:
as compared to the control group,
*$P < 0.05$,
**$P < 0.01$.

2) Test of Hyperactivity in Amfetamine Mice

Amfetamine 6 mg/kg, sc caused an increase of the number of animals with spontaneous activity by more than 2 times, haloperidol 0.1 mg/kg showed significant inhibiton effect, the number of animals with spontaneous activity was reduced to 12%, haloperidol 0.2 mg/kg showed more significant inhibition, the number of animals with spontaneous activity was only 6%, lower than that of normal animals. As for Y-QA14 20 and 30 mg/kg, the number of animals with spontaneous activity was about 75% of the model animals, the number for the 40 mg/kg group was 60% of the model animals, all showed significant inhibition (see Table 4).

TABLE 4

Effects of YQA by intraperitoneal injection on hyperactivity in amfetamine mice

| Drug | Dose (mg/kg) | Route | Animal Number | Number with spontaneous activity (M ± SD) |
|---|---|---|---|---|
| Solvent control | | ip | 8 | 358.5 ± 51.8 |
| Amfetamine control | 6 | sc | 8 | 953.8 ± 139.9# |
| Haloperidol | 0.1 | ip | 8 | 115.1 ± 65.6** |
|  | 0.2 | ip | 8 | 65.6 ± 111.7** |
| Y-QA14 | 20 | ip | 8 | 728.2 ± 225.6* |
|  | 30 | ip | 8 | 734.1 ± 202.1* |
|  | 40 | ip | 8 | 545.6 ± 221.6** |

Note:
activity increase as compared to the control,
$P < 0.05$; activity decrease as compared to amfetamine,
*$P < 0.05$,
**$P < 0.01$.

The experimental results showed that Y-QA14 can significantly inhibit the climbing behavior caused by apomorphine in mice and the hyperactivity caused by amfetamine in mice, showing Y-QA14 would have potential therapeutical effects on mental diseases.

In the above biological experiments 2-5, the compounds of other examples of the present invention also showed experimental results essentially similar to those of the compound Y-QA14.

What is claimed is:

1. A compound of formula 1,

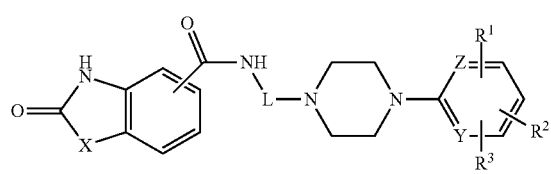

I or a tautomer, racemate, optical isomer, or pharmaceutically acceptable salt thereof, wherein:

L is —CH$_2$CH$_2$CH$_2$CH$_2$— or cis- or trans- CH$_2$CH=CHCH$_2$—;

$R^1$, $R^2$, and $R^3$ each are independently H, halogen, $C_1$-$C_6$ alkyl, substituted $C_1$-$C_6$ alkyl, $C_1$-$C_6$ alkenyl, substituted $C_1$-$C_6$ alkenyl, $C_1$-$C_6$ alkyloxy, $C_1$-$C_6$ alkylamino, di-($C_1$-$C_6$ alkyl)amino, $C_{1-10}$ hydrocarbonylcarbonyloxy, $C_{1-10}$ hydrocarbonylamido, $C_{1-10}$ hydrocarbonyloxycarbonyl, carbamoyl, or $C_{1-10}$ hydrocarbonylcarbamoyl; wherein the substituent of each group having a substituent is independently selected from halogen, hydroxyl, cyano, nitro, $C_{1-6}$ alkyl, $C_{1-6}$ alkyloxy, $C_{1-6}$ alkylthio, mono-, di- or tri-halogenated $C_{1-6}$ alkyl, amino, $C_{1-6}$ alkylamino, $C_{1-10}$ hydroxycarbonylcarbonyloxy, or $C_{1-10}$ hydrocarbonylamido;

X is O or S;

Y and Z are each independently CH or N; and the carbonyl may be at the 4-, 5-, 6-, or 7-position of the benzoxazolin-2-one or benzthiazolin-2-one ring.

2. The compound of claim 1, wherein $R^1$, $R^2$, and $R^3$ each are independently H, F, Cl, Br, I, $C_1$-$C_6$ alkyl, or $C_1$-$C_6$ alkyloxy.

3. The compound of claim 2, wherein $R^1$, $R^2$, and $R^3$ are each independently H, F, Cl, methyl, ethyl, methyloxy, or ethyloxy.

4. The compound of claim 1, wherein X is O.

5. The compound of claim 1, wherein both Y and Z are CH.

6. A compound which is selected from:
N-{4-[4-(5-chloro-2-methylphenyl)piperazinyl]butyl}-benzoxazolin-2-one-5-carboxamide;
N-{4-[4-(5-chloro-2-methylphenyl)piperazinyl]butyl}-benzoxazolin-2-one-6-carboxamide;
N-{4-[4-(2-methyloxyphenyl)piperazinyl]butyl}-benzoxazolin-2-one-5-carboxamide;
N-{4-[4-(2-methyloxyphenyl)piperazinyl]butyl}-benzoxazolin-2-one-6-carboxamide;
N-{4-[4-(5-chloro-2-methylphenyl)piperazinyl]-trans-2-buten-1-yl}-benzoxazolin-2-one-6-carboxamide;
N-{4-[4-(5-chloro-2-methylphenyl)piperazinyl]-cis-2-buten-1-yl}-benzoxazolin-2-one-5-carboxamide;
N-{4-[4-(2-methyloxyphenyl)piperazinyl]-trans-2-buten-1-yl}-benzoxazolin-2-one-5-carboxamide;
N-{4-[4-(2-methyloxyphenyl)piperazinyl]-trans-2-buten-1-yl}-benzoxazolin-2-one-6-carboxamide;
N-{4-[4-(2-methyloxyphenyl)piperazinyl]butyl}-benzothiazolin-2-one-6-carboxamide;
N-{4-[4-(5-chloro-2-methylphenyl)piperazinyl]butyl}-benzothiazolin-2-one-6-carboxamide;
N-{4-[4-(2-methyloxyphenyl)piperazinyl]-trans-2-buten-1-yl}-benzothiazolin-2-one-6-carboxamide;
N-{4-[4-(2-methyloxyphenyl)piperazinyl]butyl}-benzothiazolin-2-one-5-carboxamide; or
N-{4-[4-(5-chloro-2-methylphenyl)piperazinyl]butyl}-benzothiazolin-2-one-5-carboxamide, or a tautomer, racemate, optical isomer, or pharmaceutically acceptable salt thereof.

7. A pharmaceutical composition, comprising a compound of claim 1 and a pharmaceutically acceptable carrier or excipient.

8. A method for inhibiting dopamine D3 receptor function to treat schizophrenia, comprising-administering to a subject in need thereof an effective amount of a compound of claim 1.

9. A process for preparing a compound of claim 1, comprising the following steps:

a) converting a carboxylic acid compound of formula II:

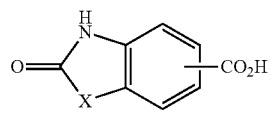

II into an acyl chloride compound of formula IIa:

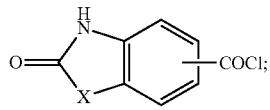

b) reacting the acyl chloride compound of formula IIa obtained in the step a) with an amine compound of formula III in the presence of a suitable base:

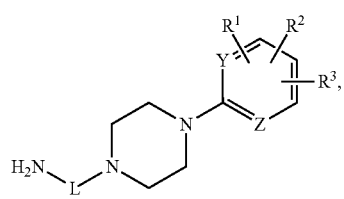

to obtain a compound of formula I:

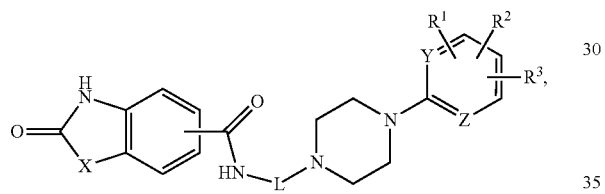

wherein

L is —$CH_2CH_2CH_2CH_2$—, cis- or trans-$CH_2CH=CHCH_2$—, or trans-cyclohexyl-4-ethyl;

$R^1$, $R^2$, and $R^3$ each are independently H, halogen, $C_1$-$C_6$ alkyl, substituted $C_1$-$C_6$ alkyl, $C_1$-$C_6$ alkenyl, substituted $C_1$-$C_6$ alkenyl, $C_1$-$C_6$ alkyloxy, $C_1$-$C_6$ alkylamino, di-($C_1$-$C_6$ alkyl)amino, $C_{1-10}$ hydrocarbonylcarbonyloxy, $C_{1-10}$ hydrocarbonylamido, $C_{1-10}$ hydrocarbonyloxycarbonyl, carbamoyl, or $C_{1-10}$ hydrocarbonylcarbamoyl; wherein the substituent of each group having a substituent is independently selected from halogen, hydroxyl, cyano, nitro, $C_{1-6}$ alkyl, $C_{1-6}$ alkyloxy, $C_{1-6}$ alkylthio, mono-, di- or tri-halogenated $C_{1-6}$ alkyl, amino, $C_{1-6}$ alkylamino, $C_{1-10}$ hydroxycarbonylcarbonyloxy, or $C_{1-10}$ hydrocarbonylamido;

X is O or S;

Y and Z are each independently CH or N; and the carbonyl may be at the 4-, 5-, 6-, or 7-position of the benzoxazolin-2-one or benzthiazolin-2-one ring.

* * * * *